United States Patent
Zigon et al.

(10) Patent No.: US 10,215,685 B2
(45) Date of Patent: Feb. 26, 2019

(54) INTERACTIVE TREE PLOT FOR FLOW CYTOMETRY DATA

(75) Inventors: Robert Zigon, Carmel, IN (US);
Rachel Vanwinkle, Lafayette, IN (US);
Jeremy Alan Smith, Indianapolis, IN (US); Larry Myers, Greenfield, IN (US)

(73) Assignee: Beckman Coulter, Inc., Brea, CA (US)

( * ) Notice: Subject to any disclaimer, the term of this patent is extended or adjusted under 35 U.S.C. 154(b) by 1025 days.

(21) Appl. No.: 12/557,144

(22) Filed: Sep. 10, 2009

(65) Prior Publication Data
US 2010/0070904 A1    Mar. 18, 2010

Related U.S. Application Data

(60) Provisional application No. 61/097,493, filed on Sep. 16, 2008.

(51) Int. Cl.
| | |
|---|---|
| *G01N 15/14* | (2006.01) |
| *G06K 9/62* | (2006.01) |
| *G06F 19/26* | (2011.01) |

(52) U.S. Cl.
CPC .......... *G01N 15/147* (2013.01); *G06F 19/26* (2013.01); *G06K 9/6219* (2013.01);
(Continued)

(58) Field of Classification Search
CPC .......................... G06T 11/206; G06K 9/6219; G06K 9/00147; G06K 9/00127; G06K 9/6253;
(Continued)

(56) References Cited

U.S. PATENT DOCUMENTS

| | | | |
|---|---|---|---|
| 4,845,653 A | | 7/1989 | Conrad et al. |
| 5,234,816 A | * | 8/1993 | Terstappen ....... G01N 33/56977 435/7.24 |

(Continued)

FOREIGN PATENT DOCUMENTS

| | | |
|---|---|---|
| EP | 1 770 387 A2 | 4/2007 |
| JP | 2006-208390 A | 8/2006 |

(Continued)

OTHER PUBLICATIONS

Wikipedia, "Flow cytometry", http://en.wikipedia.org/wiki/Flow_cytometry dated Nov. 17, 2007, https://web.archive.org/web/20071117125740/http://en.wikipedia.org/wiki/Flow_cytometry#Fluorescence-activated_cell_sorting, printout pp. 1-5.*

(Continued)

*Primary Examiner* — Amy Ng
*Assistant Examiner* — William Wong
(74) *Attorney, Agent, or Firm* — K&L Gates LLP; Louis C. Cullman; Andrew L. Reibman

(57) ABSTRACT

Methods, systems, and computer program products can be used for displaying and analyzing data. A method operates by receiving and displaying flow cytometry data in a tree plot, which represents multiple variations of classified flow cytometry data within an interface of computer that includes an input device. The interface permits a user to select, using the input device, portions of the tree plot associated with characteristics and sub-sets of the data. In an example, one or more histograms, contour plots, density plots, radar plots, and scatter plots representing the data are displayed within the interface. The interface permits a user to select, using the input device, portions of the histograms, contour plots, density plots, radar plots, and scatter plots, corresponding to characteristics and sub-sets of the data. In an example, updated histograms and plots are displayed in the interface (Continued)

substantially immediately based upon selected characteristics and subsets of the data.

23 Claims, 23 Drawing Sheets

(52) U.S. Cl.
CPC ... *G06K 9/6253* (2013.01); *G01N 2015/1477* (2013.01); *G01N 2015/1488* (2013.01)

(58) Field of Classification Search
CPC .......... G06F 19/26; G06F 19/24; G06F 19/20; G06F 3/0481; G06F 3/04817; G06F 3/0482; G06F 19/18; G01N 15/147; G01N 2015/1477; G01N 2015/1488
USPC ........................... 715/771, 853–855; 702/21
See application file for complete search history.

(56) References Cited

U.S. PATENT DOCUMENTS

| | | | |
|---|---|---|---|
| 5,325,493 A | 6/1994 | Herrell et al. | |
| 5,734,791 A * | 3/1998 | Acero | G10L 19/038 704/200 |
| 5,739,000 A * | 4/1998 | Bierre | G01N 33/5094 435/2 |
| 5,894,311 A * | 4/1999 | Jackson | 345/440 |
| 6,009,372 A * | 12/1999 | Baker | F02D 41/2425 701/115 |
| 6,014,904 A * | 1/2000 | Lock | 73/865.5 |
| 6,100,901 A | 8/2000 | Mohda et al. | |
| 6,111,578 A * | 8/2000 | Tesler | G06T 11/206 345/419 |
| 6,178,382 B1 | 1/2001 | Roederer et al. | |
| 6,203,987 B1 * | 3/2001 | Friend | C12Q 1/6809 435/6.13 |
| 6,274,342 B1 * | 8/2001 | Gutierrez-Ramos et al. | 435/69.5 |
| 6,373,483 B1 | 4/2002 | Becker et al. | |
| 6,381,605 B1 * | 4/2002 | Kothuri et al. | |
| 6,415,175 B1 * | 7/2002 | Conley et al. | 600/523 |
| 6,421,072 B1 * | 7/2002 | Ku | G06F 3/0482 715/804 |
| 6,462,762 B1 * | 10/2002 | Ku | G06F 3/0481 707/E17.01 |
| 6,496,208 B1 * | 12/2002 | Bernhardt et al. | 715/853 |
| 6,535,819 B1 * | 3/2003 | Clark | 702/19 |
| 6,615,141 B1 * | 9/2003 | Sabry et al. | 702/19 |
| 6,738,502 B1 * | 5/2004 | Coleman et al. | 382/133 |
| 6,868,525 B1 * | 3/2005 | Szabo | G06F 17/30067 705/14.53 |
| 7,315,785 B1 * | 1/2008 | Nozaki et al. | 702/19 |
| 2001/0049678 A1 * | 12/2001 | Yaginuma | 707/3 |
| 2002/0070953 A1 * | 6/2002 | Barg et al. | 345/700 |
| 2002/0085039 A1 * | 7/2002 | Blower et al. | 345/776 |
| 2002/0155420 A1 * | 10/2002 | Vaisberg et al. | 435/4 |
| 2002/0155480 A1 * | 10/2002 | Golub et al. | 435/6 |
| 2002/0160401 A1 * | 10/2002 | Nozaki et al. | 435/6 |
| 2002/0171646 A1 | 11/2002 | Kandogan | |
| 2003/0105771 A1 * | 6/2003 | Tiefenbrun et al. | 707/103 R |
| 2003/0128212 A1 * | 7/2003 | Pitkow | 345/440 |
| 2003/0147859 A1 * | 8/2003 | Reisner | 424/93.7 |
| 2003/0187716 A1 * | 10/2003 | Lee | 705/10 |
| 2003/0218634 A1 * | 11/2003 | Kuchinsky et al. | 345/764 |
| 2003/0219818 A1 * | 11/2003 | Bohen et al. | 435/6 |
| 2003/0235919 A1 * | 12/2003 | Chandler | 436/43 |
| 2004/0153247 A1 * | 8/2004 | Czernuszenko et al. | 702/14 |
| 2004/0162679 A1 * | 8/2004 | Li | 702/20 |
| 2004/0241759 A1 * | 12/2004 | Tozer et al. | 435/7.2 |
| 2005/0165766 A1 * | 7/2005 | Szabo | 707/3 |
| 2005/0214316 A1 * | 9/2005 | Brown | C07K 14/005 424/186.1 |
| 2005/0223024 A1 * | 10/2005 | Hyun | G06F 17/30126 |
| 2005/0228041 A1 * | 10/2005 | Sen et al. | 514/458 |
| 2006/0003391 A1 * | 1/2006 | Ring | G01N 33/57415 435/7.23 |
| 2006/0008803 A1 * | 1/2006 | Brunner et al. | 435/6 |
| 2006/0020398 A1 * | 1/2006 | Vernon et al. | 702/20 |
| 2006/0047501 A1 * | 3/2006 | Seroussi | H03M 7/40 704/9 |
| 2006/0073474 A1 * | 4/2006 | Perez et al. | 435/6 |
| 2006/0263833 A1 | 11/2006 | Loken et al. | |
| 2006/0282443 A1 * | 12/2006 | Hanagata | G06F 17/3028 |
| 2006/0288311 A1 * | 12/2006 | Heer | G06T 11/206 715/853 |
| 2007/0003922 A1 * | 1/2007 | Amaral et al. | 435/4 |
| 2007/0020691 A1 * | 1/2007 | Kanter et al. | 435/7.1 |
| 2007/0185656 A1 * | 8/2007 | Schadt | G01N 33/5023 702/19 |
| 2007/0185904 A1 * | 8/2007 | Matsuzawa et al. | 707/104.1 |
| 2008/0020379 A1 * | 1/2008 | Agan et al. | 435/6 |
| 2008/0052623 A1 * | 2/2008 | Gutfleisch | G06F 3/0482 715/713 |
| 2008/0263468 A1 * | 10/2008 | Cappione et al. | 715/771 |
| 2008/0305962 A1 * | 12/2008 | Wirtz | C12Q 1/6886 506/9 |
| 2009/0007127 A1 | 1/2009 | Roberts et al. | |
| 2009/0164171 A1 * | 6/2009 | Wold | G06F 17/18 702/179 |
| 2009/0327240 A1 * | 12/2009 | Meehan et al. | 707/3 |
| 2010/0054554 A1 * | 3/2010 | Dutta et al. | 382/128 |
| 2010/0062471 A1 * | 3/2010 | Kantor et al. | 435/29 |

FOREIGN PATENT DOCUMENTS

| | | |
|---|---|---|
| WO | WO 99/58955 A1 | 11/1999 |
| WO | WO 2007/117423 A2 | 10/2007 |
| WO | WO 2008/052258 A1 | 5/2008 |

OTHER PUBLICATIONS

Perfetto et al., "Seventeen-colour flow cytometry: unravelling the immune system", Nature Reviews Immunology 4, Aug. 2004, pp. 648-655.*
"Flow Cytometry and Cell Sorting Facility", Clinimmune Labs, Flow Cytometry, University of Colorado at Denver and Health Sciences Center, Jun. 6, 2008, http://www.uchsc.edu/clinimmune/flowcytometry/index.htm, 3 pgs.
"How Many Threads Does it Take to Screw in the Lightbulb?", The Daily Dongle: On the Thread of Threading, Aug. 29, 2008, 2 pgs, http://flowjo.typepad.com/the_daily_dongle/2008/08/on-the-thread-of-threading.html.
"NVIDIA CUDA Compute Unified Device Architecture: Programming Guide" Version 1.1, Nov. 29, 2007, 143 pgs.
"VenturiOne™: built for speed and simplicity", Flow Cytometry Analysis from Applied Cytometry and VenturiOne/StarStation, Feb. 11, 2008, 1 pg, http://www.appliedcytometry.com/venturi.php.
Buck et al., "Data Parallel Computation on Graphics Hardware", Stanford University, Jan. 2003, 9 pgs.
Cates et al., "GIST: An Interactive, GPU-Based Level Set Segmentation Tool for 3D Medical Images", School of Computing University of Utah, Feb. 27, 2004, 28 pgs.
FlowJo Manual, Flow Cytometry Analysis Software, Tree Star, Inc. 2007, file:///Users/tom/FlowJo%20fWebsite/v7%20print/v7/html, 229 pgs.
Frishman, Yaniv, "Multi-Level Graph Layout on the GPU", IEEE, Nov. 2007, 8 pgs.
Kandogan, Eser, "Star Coordinates: A Multi-dimensional Visualization Technique with Uniform Treatment of Dimensions", IBM Almaden Research Center, 1998, 4 pgs.
Murdoch, Andrew A., "Potential of Commodity Graphics Hardware for Scientific Computation", EPCC, The University of Edinburgh, Nov. 5, 2002, 19 pgs.
Nvidia CUDA Zone webpage, Nvidia Corporation, Jun. 11, 2008, http://www.nvidia.com/object/cuda_home.html, 2 pgs.
Nvidia Geforce 8 Series webpage, Nvidia Corporation, Jun. 11, 2008, http://www.nvidia.com/page/geforce8.html, 3 pgs.

(56) References Cited

OTHER PUBLICATIONS

Perfetto et al., "Seventeen-colour flow cytometry: unravelling the immune system" *Nature Reviews*, Immunology, Perspectives, www.nature.com/reviews/immunol, Aug. 2004, vol. 4, pp. 648-655.

Stohr et al., "Visualization of Multidimensional Spectra in Flow Cytometry" Multidimensional Spectra in Flowcytometry, *The Jornal of Histochemistry and Cytochemistry*, The Histochemical Society Inc., Jun. 16, 1978, vol. 27, No. 1, pp. 560-563.

Venkatasubramanian, Suresh, "The Graphics Card as a Stream Computer", AT&T Labs—Research, Oct. 7, 2003, 3 pgs.

Zigon et al., "Extensible Data Warehouse for Flow Cytometry Data", U.S. Appl. No. 12/211,582, filed Sep. 16, 2008.

Zigon et al., "Collision Free Hash Table for Classifying Data", U.S. Appl. No. 12/211,794, filed Sep. 16, 2008.

\* cited by examiner

INTERACTIVE TREE PLOT FOR FLOW CYTOMETRY DATA

CROSS-REFERENCE TO RELATED APPLICATIONS

The present application claims the benefit of U.S. Provisional Appl. No. 61/097,493; filed Sep. 16, 2008, which is incorporated by reference herein in its entirety.

BACKGROUND

Field

The present invention is generally directed to displaying and analyzing data, and more particularly directed to displaying and analyzing data from biological sample analyzers, such as flow cytometer instruments.

Background

Many researchers need to analyze and plot large amounts of data, e.g., multidimensional data. For example, a system which generates large amounts of data may be a biological sample analyzer, such as a flow cytometer instrument. Flow cytometers are widely used for clinical and research use. A biological mixture may comprise a fluid medium carrying a biological sample such as a plurality of discrete biological particles, e.g., cells, suspended therein. Biological samples can include blood samples or other cells within a heterogeneous population of cells. Information obtained from the biological particles is often used for clinical diagnostics and/or data analyses.

Flow cytometry is a technology that is used to simultaneously measure and analyze multiple parameters (e.g., physical characteristics or dimensions) of particles, such as cells. Flow cytometry analysis includes techniques for analyzing multiple parameters. Parameters (e.g., characteristics, properties, and dimensions) measurable by flow cytometry include cellular size, granularity, internal complexity, fluorescence intensity, and other features. Some parameters may be measurable after adding a marker. For example, fluorochrome-conjugated antibodies may emit photons of light in an identifiable spectrum upon excitation of the fluorochrome. Detectors are used to detect forward scatter, side scatter, fluorescence, etc. in order to measure various cellular properties. Cellular parameters identified by flow cytometer instruments can then be used to analyze, identify, and/or sort cells.

In traditional flow cytometry systems, a flow cytometer instrument is a hardware device used to pass a plurality of cells singularly through a beam of radiation formed by a light source, such as a laser beam. A flow cytometer instrument captures light that emerges from interaction(s) with each of the plurality of cells as each cell passes through the beam of radiation.

Currently available flow cytometry systems may include three main systems, i.e., a fluidic system, an optical system, and an electronics system. The fluidic system may be used to transport the particles in a fluid stream past the laser beam. The optical system may include the laser that illuminates the individual particles in the fluid stream, optical filters that filter the light before or after interacting with the fluid stream, and the photomultiplier tubes that detect the light beam after the light passes through the fluid stream to detect, for example, fluorescence and/or scatter. The electronic system may be used to process the signal generated by the photomultiplier tubes or other detectors, convert those signals, if necessary, into digital form, store the digital signal and/or other identification information for the cells, and generate control signals for controlling the sorting of particles. The data point having the parameters corresponding to the measurement of one cell or other particle is termed an event. In traditional flow cytometry systems, a computer system converts signals received from detectors such as light detectors into digital data that is analyzed.

Flow cytometry systems capture large amounts of data from passing thousands of cells per second through the laser beam. Subpopulations of captured flow cytometry data must be selected and gated (e.g., by drawing a gate on a displayed graph or plot) so that statistical analysis can subsequently be performed on the data. Since flow cytometers operate at very high speeds and collect large amounts of data in short amounts of time, it is necessary for the data display and analysis systems to operate at very high speeds and to graphically depict the data efficiently. Statistical analysis of the data can be performed by a computer system running software that generates reports on the characteristics of selected subpopulations (i.e., gates) of the cells, wherein the cellular characteristics include one or more of cellular size, mitotic phase, cellular complexity, phenotype, and health.

Many conventional flow cytometry systems depict data as series of individual scatter plots (i.e., dot plots) or histograms. Two dimensional dot plots are not well suited for near instantaneous analysis and display of large amounts of data. Although many report-writing tools exist for polychromatic flow cytometry data, these traditional tools do not allow users to interactively display hierarchical, iterative tree plots that summarize large flow cytometry data sets. Accordingly, what is needed are methods, systems, and computer program products that allow users to alter and fine-tune graphs depicting flow cytometry data interactively, dynamically adjusting views of the data, even in cases where the graphs represent large amounts of data.

Traditional flow cytometry analysis tools do not allow users to interactively alter plots representing flow cytometry data on an ad-hoc basis such that the plots are updated substantially immediately. Flow cytometry list mode files are files containing raw flow cytometry data, such as FCS files. As used herein, an FCS file refers to a flow cytometry data file compliant with the International Society for Advancement of Cytometry (ISAC) Flow Cytometry Standard (FCS).

There are technical challenges involved in analyzing and graphically depicting large amounts of Polychromatic Flow Cytometry data. In traditional systems, as flow cytometry datasets increase in size, there is a corresponding degradation in data display and statistical analysis performance.

Flow cytometry systems capture large numbers of events from passing thousands of cells per second through the laser beam. Captured flow cytometry data is stored so that statistical analysis can subsequently be performed on the data. Typically, flow cytometers operate at high speeds and collect large amounts of data. Statistical analysis of the data can be performed by a computer system running software that generates reports on the characteristics (i.e., dimensions) of the cells, such as cellular size, complexity, phenotype, and health. Polychromatic flow cytometry refers to methods to analyze and display complex multi-parameter data from a flow cytometer instrument. Polychromatic flow cytometry data may include many parameters. Conventional flow cytometry systems depict this data as series of graphs, such as scatter plots and histograms, to aid operator analysis of the data. These conventional flow cytometry systems encounter difficulties efficiently depicting polychromatic flow cytometry data containing 6 or more colors. These conventional systems also do not allow users, such as researchers, flow cytometrists, and clinicians to interact with the scatter plots and histograms in order to select subpopulations or 'gates' of data to be depicted in new and updated interactive plots which are substantially immediately generated and updated.

Scatter plots and histograms are the common visualization and analysis tools used by flow cytometrists and clinicians. The number of bivariate scatter plots that can be generated for a cytometry protocol with N fluorochromes is $(N \times (N-1))/2$ and the number of univariate plots is N. If, for example, a protocol has 5 fluorochromes, then the number of scatter plots that can be generated is $(5 \times 4)/2$ or 10. When 18 color protocols are used $(18 \times 17)/2$ or 153 scatter plots can be generated. Flow cytometrists, researchers, and clinicians experience difficulties assimilating and analyzing information from large numbers of scatter plots. For example, it is difficult for users to readily identify biologically significant events within 153 scatter plots.

There are difficulties and challenges associated with displaying, visualizing, and analyzing polychromatic flow cytometry data. These challenges increase with data generated by 6 or more fluorochromes. Traditional analysis and display tools do not readily reveal the biological significance of event data in a manner that allows users and clinicians to iteratively update a related set of interactive plots. Accordingly, what is needed are methods and systems that allow display and analysis of large amounts of polychromatic flow cytometry data.

SUMMARY

Methods, systems, and computer program products for displaying and analyzing classified data using a graphical user interface (GUI) are disclosed. In an embodiment, the method operates by receiving and displaying flow cytometry data in a tree plot representing multiple variations of classified flow cytometry data. The method displays the tree plot within an interface. The interface permits a user to select, using an input device, portions of the tree plot associated with characteristics and sub-sets of the data. One or more histograms, contour plots, density plots, radar plots, and scatter plots representing the data are displayed within the interface. The interface permits a user to select portions of the histograms, contour plots, density plots, radar plots, and scatter plots, corresponding to characteristics and sub-sets of the data. The selections are made via use of an input device. Updated histograms and plots are displayed in the interface based upon selected characteristics and subsets of the data. In one embodiment, the updated histograms and plots are generated and displayed in the interface substantially immediately.

In another embodiment, a system generates, within a GUI, an interactive tree plot that graphically represents multiple variations of phenotypic classifiers for captured polychromatic flow cytometry data. The system builds and displays interactive tree plots in an interface which allows users to select subsets of displayed flow cytometry data. The system represents the flow cytometry data as one or more histograms, contour plots, density plots, radar plots, scatter plots, and tree plots. The system generates updated and new plots corresponding to user-selected subsets of the displayed flow cytometry data. In an embodiment, a tree plot which graphically represents multiple variations of classified flow cytometry data, is displayed within an interface of a computer device that includes an input device. The interface permits a user to select, using the input device, portions of the tree plot associated with characteristics and sub-sets of the flow cytometry data. In another embodiment, the system generates and displays one or more histograms, contour plots, density plots, radar plots, and scatter plots representing received flow cytometry data within the interface. The user interface of the system permits a user to select, using the input device, portions of the histograms, contour plots, density plots, radar plots, and scatter plots, wherein the portions correspond to characteristics and sub-sets of the received flow cytometry data. In an embodiment, updated tree plots, histograms, contour plots, density plots, radar plots, and scatter plots are displayed in the interface based upon selected characteristics and subsets of received flow cytometry data.

Further features and advantages of the present invention, as well as the structure and operation of various embodiments thereof, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS/FIGURES

The accompanying drawings, which are incorporated herein and form part of the specification, illustrate the embodiments of present invention and, together with the description, further serve to explain the principles of the invention and to allow a person skilled in the relevant art(s) to make and use the invention.

Figure 1:
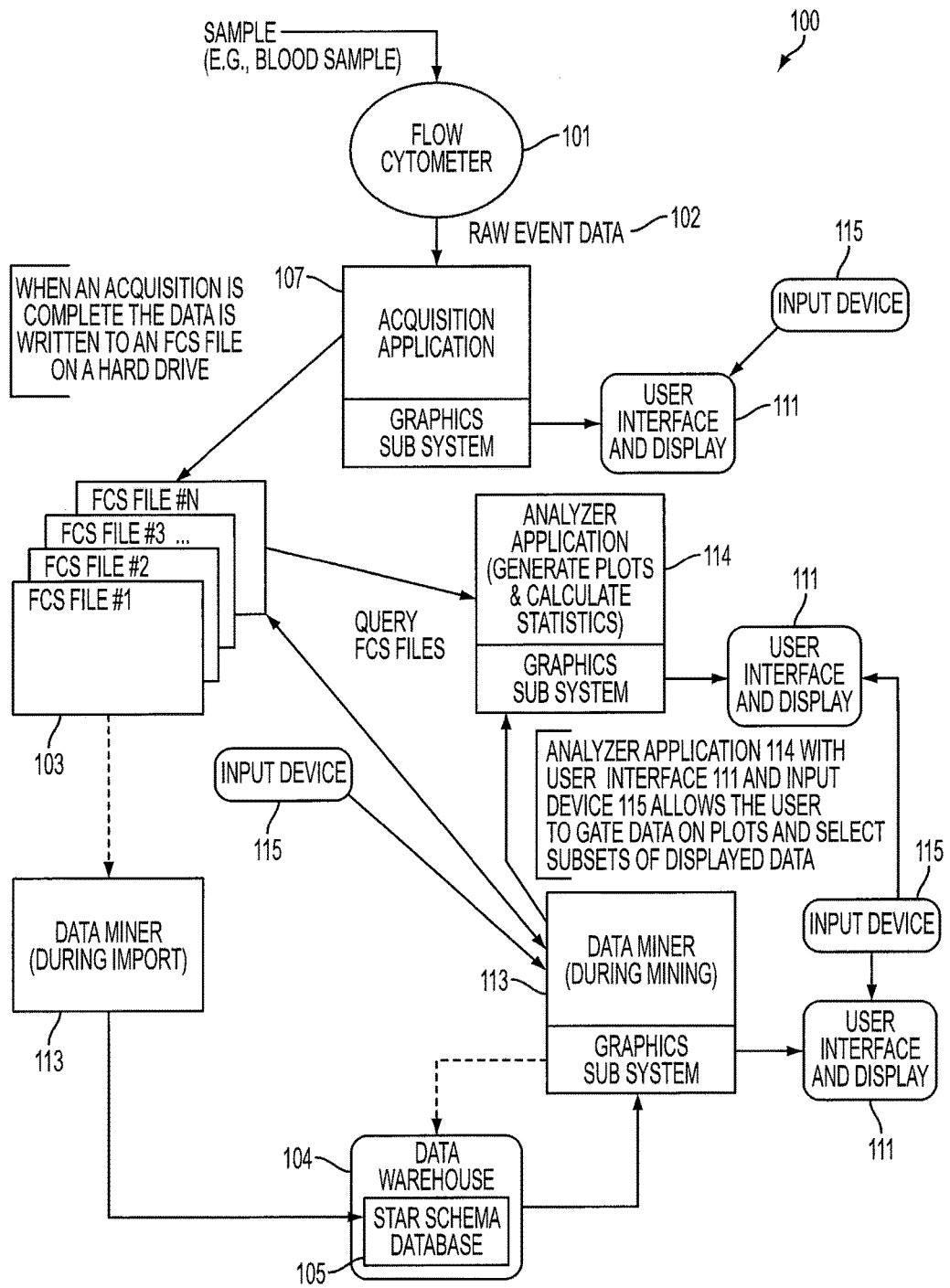
FIG. 1 illustrates a high-level diagram of a flow cytometry data display and analysis system, according to an embodiment of the invention.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art based on the teachings contained herein.

DETAILED DESCRIPTION

1. Overview of the Invention . . . 7
2. Components of the Data Display and Analysis System . . . 12
    (a) Flow Cytometry Data Analysis . . . 12
3. Graphs and Gating of Displayed Data . . . 15
    (a) Scatter Plots . . . 15
    (b) Gating Displayed Data . . . 16
    (c) Histograms . . . 19
    (d) Interactive Tree Plot . . . 20
    (e) Other Plots . . . 21
4. Tree Plot Data Generation . . . 22
5. Exemplary Data Analysis with the User Interface . . . 24
6. Data Display and Analysis Method . . . 31
7. Example Computer Implementation . . . 32

1. Overview of the Invention

This specification discloses one or more embodiments that incorporate the features of this invention. The disclosed embodiment(s) merely exemplify the invention. The scope of the invention is not limited to the disclosed embodiment(s). The invention is defined by the claims appended hereto.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

The description of "a" or "an" item herein may refer to a single item or multiple items. For example, the description of a component, a characteristic, an input device, a plot, a gate, a database, a user, a marker, a dye, a branch, a leaf, or a file may refer to a single component, characteristic, input device, plot, gate, a database, a user, a marker, a dye, a branch, a leaf, or a file. Alternatively, the description of a component, a characteristic, an input device, a plot, a gate, a database, a user, a marker, a dye, a branch, a leaf, or a file may refer to multiple components, characteristics, input devices, plots, gates, databases, users, markers, dyes, branches, leaves, or files. Thus, as used herein, "a" or "an" may be singular or plural. Similarly, references to and descriptions of plural components may refer to single items or components.

Embodiments of the invention may be implemented in hardware, firmware, software, or any combination thereof. Embodiments of the invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of propagated signals (e.g., carrier waves, infrared signals, digital signals, etc.), and others. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

Embodiments of the present invention disclosed herein display and analyze amounts of biological sample data from a flow cytometer instrument in a graphical user interface. The system embodiments disclosed herein are configured to allow for dynamically updating scatter plots, histograms, contour plots, density plots, contour plots, and tree plots when new subpopulations of data are selected as a result of user interaction with a user interface.

Embodiments of the present invention provide various methods that use graphing and statistical techniques for biological sample analysis and reporting applications. Such methods may be used, for example, in flow cytometry systems. Exemplary flow cytometry systems suitable for use in the present invention include any of the polychromatic (5 or more color) instruments presently on the market or currently in development. Instruments presently on the market wherein embodiments of the present invention can be implemented on include the CyAN™ ADP Analyzer series of instruments manufactured and sold by BECKMAN COULTER (Fullerton, Calif.). Polychromatic flow cytometers are also available from Becton Dickinson, such as the BD FACSCanto™ II system, and others.

It is understood that a hematology analyzer is a specialized form of a flow cytometry system. Thus, in at least some embodiments, the flow cytometry system is a hematology analyzer. Thus, the flow cytometry data can be hematology analyzer data.

For example, the present invention includes system, method, and computer program product embodiments for displaying, graphically depicting, and analyzing large amounts of flow polychromatic cytometry data. Embodiments of the invention include a unique GUI which allows interaction between a plurality of related plots and graphs.

Embodiments of the invention also include a user interface that allows users to dynamically update tree plots and plots related to the tree plots, e.g., via drag and drop operations performed on portions (e.g., branches and leaves) of the tree plots. In an embodiment, leaves in an interactive tree plot can be used as an input gate for another plot, such as a histogram, a scatter plot, a contour plot, a radar plot, or a density plot. According to an embodiment, branches of a tree plot can have multiple leaves within a bin of data.

The present invention includes system, method, and computer program product embodiments for displaying and analyzing polychromatic flow cytometry data.

Embodiments of the present invention include methods and systems that allow a researcher to investigate upwards of 512 phenotypes (i.e., 9 or more fluorochromes) with a single, interactive tree plot. The systems and methods allow a researcher to use multiple plots, each with respective markers, wherein the plots are related to each other and selections of subpopulations of data depicted in one plot can be used as gates in another plot in order to view upwards of 1024 phenotypes.

Embodiments include methods and systems to generate interactive histograms and tree plots in a user interface. In the case of histograms and tree plots, each event may be classified or "binned" according to certain attributes of the event. The process for classifying flow cytometry data is explained in more detail in U.S. patent application Ser. No. 12/211,794, entitled "Collision Free Hash Table for Classifying Data," filed Sep. 16, 2008, by Zigon et al., which is incorporated by reference herein in its entirety.

Embodiments of the invention may be used in and/or include a serial (non-parallel) processing environment or in a parallel processing environment. For example, certain embodiments of the invention apply to and/or include the parallel processing architectures: Single Instruction Multiple Data (SIMD), Single Process Multiple Data (SPMD), and/or Single Instruction Multiple Thread (SIMT). Flow cytometry analysis is particularly suited to architectures such as these as they are particularly suited to the performance of an operation or process on a large number of data points and events. A parallel processing architecture for flow cytometry may be optimized through use of a multiple-processor chip, such as a graphical processing unit, instead of or in addition to a single or dual processing chip, such as a more traditional central processing unit (CPU). For example, a graphics card as manufactured by NVIDIA of Santa Clara, Calif. or by ATI/AMD of Sunnyvale, Calif. may be used as part of computer system 2200 described below with reference to FIG. 22.

Example embodiments, such as those using an NVIDIA Graphics Processing Unit (GPU) having 128 Processing Elements (e.g., certain 8800 series products), using the techniques herein may process five million event-parameters of captured data (e.g., captured flow cytometry data) in less than 5 seconds, preferably less than 2 seconds and most preferably less than 1 second. One hundred million to one billion (preferably at least 500 million, most preferably at least 750 million) event-parameters may be processed in less than 30 seconds, preferably less than 15 seconds and most preferably less than 5 seconds. Event parameters are the number of events multiplied by the number of parameters in each event. As hardware technology progresses, the performance of embodiments of this invention will continue to likewise improve. Similarly, improvements to operating systems and other software that yield general performance gains will also improve the performance of embodiments of this invention.

Because of the large number of events typically processed, the display, iterative plot generation, and analysis process using traditional systems and methods takes a significant amount of time, slowing analysis, and frustrating users. An advantage of embodiments of the invention are that they provide methods and systems that allow the rapid display of classified data as a set of related, interactive plots and graphs.

Although the present specification describes user-selected input gates, characteristics, and subpopulations of displayed data, users can be people, computer programs, software applications, software agents, macros, etc. Besides a human user who needs to view and analyze data, a software application or agent sometimes needs to access data. Accordingly, unless specifically stated, the term "user" as used herein does not necessarily pertain to a human being.

Embodiments of the present invention provide systems, methods, and computer program products for displaying and analyzing large amounts of data. For example, these embodiments are shown in FIGS. 3-22 below.

Also, in another embodiment, a system that generates plots and graphs based upon graphically-selected input gates of displayed data is presented. For example, the system depicts user-selected input gates in an interactive tree plot.

For example, these embodiments are shown in FIGS. 4-22 below. The system in this embodiment includes a graphical user interface (GUI) that allows users to select portions of displayed, plotted data, and analyze the displayed data via drag-and-drop operations within the GUI.

2. Components of the Data Display and Analysis System

FIG. 1 illustrates a flow cytometry data display and analysis system 100, in accordance with an embodiment of the invention. System 100 displays and allows analysis of data received from a flow cytometer 101, FCS files 103, and/or a data warehouse 104 including a star schema database 105. The flow cytometry data is acquired by an acquisition application 107 for subsequent analysis by an analysis application 108. Analyzer application 114 includes a graphics sub-system, and works in conjunction with user interface 111 and input device 115. Analyzer application 114 is used to analyze data imported by data import application 113 (e.g., a data import device). An exemplary detailed view of analyzer application 114 and user interface 111 is shown in FIGS. 4-22, discussed in Section 5 below.

Data warehouse 104 can be used to store and manage raw event data 102 received from either flow cytometer 101 or acquisition application 107. User interface 111 can allow users, such as clinicians and scientists, to choose which FCS files 103 to analyze and plot via analyzer application 114.

Analyzer application 114 can allow users to control, via user interface 111, which data to be displayed as histograms, scatter plots, contour plots, radar plots, density plots, and tree plots. Analyzer application 114 can allow users perform a series of iterative plot updates by selecting gates of displayed data within user interface 111 in order to facilitate analysis of the updated plots. Analysis results can be displayed using analyzer application 114 based upon data from data warehouse 104 and displayed on user interface 111 under control of analyzer application 114.

(a) Flow Cytometry Data Analysis

A simplified flow cytometry data analysis process is described in this section. In an embodiment, flow cytometry data is received from a data source. The data source may be raw data files, such as, but not limited to FCS files 103 compliant with the ISAC standard, a database, a data warehouse, a data store, data query results from data miner 113, or directly from an instrument such as flow cytometer 101. For example, a data miner and data warehouse is explained in more detail in U.S. patent application Ser. No. 12/211, 582, entitled "Extensible Data Warehouse for Flow Cytometry Data," filed Sep. 16, 2008, by Zigon et al., which is incorporated by reference herein in its entirety.

Flow cytometry data can be viewed as an M×N matrix of M events and N parameters, where M and N are positive integers equal or greater than 0. When viewing a displayed graph (e.g., on a screen or printed page), the range of the data can reduce the effectiveness of the display. For example, a parameter may have a range of possible parameter values from 0 to 1,000,000, but a data set may have actual values in the range of 100 to 500. Thus, displaying the full scale axis on a 100 pixel square dot plot would force the entire data set to a single pixel row or column. Thus, the data needs to be transformed to provide a viewer with an accurate representation. In various examples, parameter values may be transformed to a linear scale or a logarithmic scale. Linear transformation may be performed by computing a new parameter value from the original parameter value using the equation y=a*x+b, where x is the old value, y is the new value, and a and b are constants. Logarithmic transformation may be performed by computing a new parameter value form the original parameter value using the equation y=b*log(a*x), where x is the old value, y is the new value, a and b are constants, and log is a logarithm of any base. In one example, all of the events in the data are sequentially or serially traversed for the particular parameter to be transformed resulting in an O(n) operation, where n is the number of events.

In an embodiment of the present invention, plots are generated. For example, plots for a graphical representation of the data to be shown on user interface 111 through a graph or through a hard copy output (i.e., to a paper printer or plotter). There are various types of plots that may be generated. For example, plots that can be generated are, but are not limited to, dot plots, density plots, scatter plots, radar plots, and tree plots, which may be generated by analyzer application 114. For example, analyzer application may scan a data set including FCS files 103 or data from data miner 113 to determine the pixel(s) corresponding to the parameter value(s) of each event to be graphically displayed. In histograms and tree plots, the data set is scanned and the requisite counters are incremented. These counters may be visualized by drawing leaves of corresponding heights. Generation of some of these types of plots is described in more detail herein.

In accordance with an embodiment of the invention, statistics corresponding to data depicted in a tree plot are determined. For example, a user may select mean, median, mode, standard deviation etc., to describe the data displayed in a tree plot. Statistics may be determined for the entire data set or on user-selected sub-populations (e.g., median value of parameter x for all the events inside gate A).

According to an embodiment of the present invention, plots and/or statistics are displayed. For example, plots and/or statistics may be displayed on any media (e.g., a computer screen display such as user interface 111) for the user. Although underlying processing, determining, decision making, and/or calculations resolving various aspects of the displaying flow cytometry data are important, some embodiments of the invention herein are not concerned with processing of the data per se. For example, processing, decision making, and calculations resolving aspects of displaying flow cytometry data are explained in more detail in U.S. Provisional Patent Application No. 61/097,519, entitled "Race Condition Avoidance for Controlling Output of Data," filed Sep. 16, 2008, by Zigon et al., which is incorporated by reference herein in its entirety. Rather, these embodiments of the invention described herein are concerned with display of data for analysis, and an interface allowing use of the displayed data in flow cytometry systems. Thus, when discussing determining a pixel or pixel value, the term pixel and pixel value refers to a potential specific location on a display, such as user interface 111, and not a corresponding memory location or other storage area. Further, an attribute, such as shape, may be used to convey information to a user. In that case, a pixel would not be a pixel in the ordinary sense of the term, but instead would be a discrete location include a set of pixels on a display, such as user interface 111, thus the location may include more than one pixel in the ordinary sense.

According to an embodiment, gating of data is performed by a user via use of input device 115 to interact with plotted data displayed in user interface 111. Gating is discussed in detail elsewhere herein. For example, a user may manipulate graphical displays of gates (e.g., click and drag or otherwise draw a gate on a displayed graph or plot using input device 115) or use any other method of describing a gate to the system, including having default gates. Additionally, or alternatively, after completion of the gating process, plots and corresponding statistical reports may be updated by re-transforming the data, re-generating the plots, and/or re-computing statistics. Plot updating processes may be repeated (i.e., iterated) for all displayed data or only for the data affected by the gating.

Thus, according to one or more embodiments, the flow cytometry analysis processes described herein allow the user to iteratively analyze and display the data by selecting and/or modifying the types of graphs displayed and the variables, axes, and/or gates of interest.

3. Graphs and Gating of Displayed Data

In this section, various interactive graphs and plots, such as tree plots, are described. In embodiments of the present invention, the graphs described in this section are generated and displayed within a graphical user interface (GUI) and users are able to interact with the graphs displayed within the GUI through use of an input device. This section in no way should be seen as an exhaustive discussion of all graph and plot types available for display, but rather exemplary graphs and plots, as would be understood by a skilled artisan.

(a) Scatter Plots

Figure 2B:
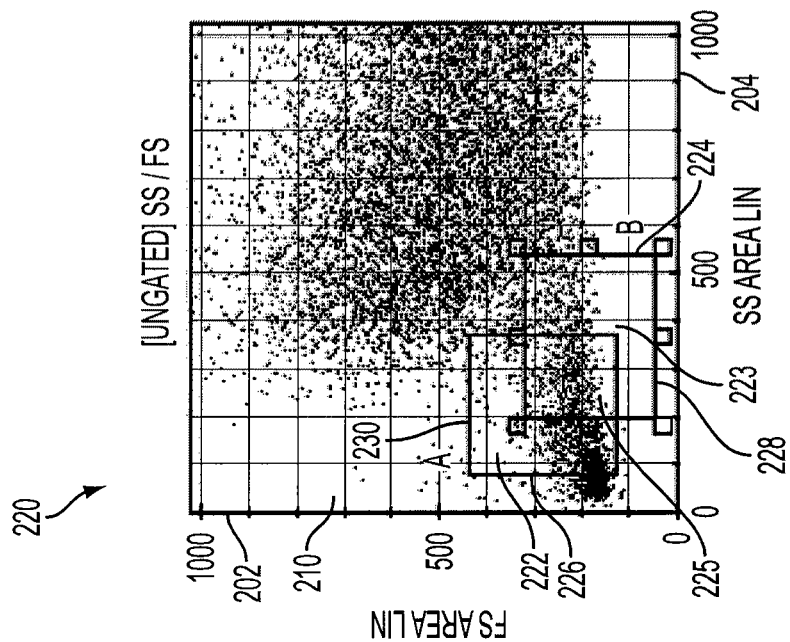
FIG. 2B illustrates an exemplary two dimensional scatter plot graph with multiple gates.
Figure 2A:
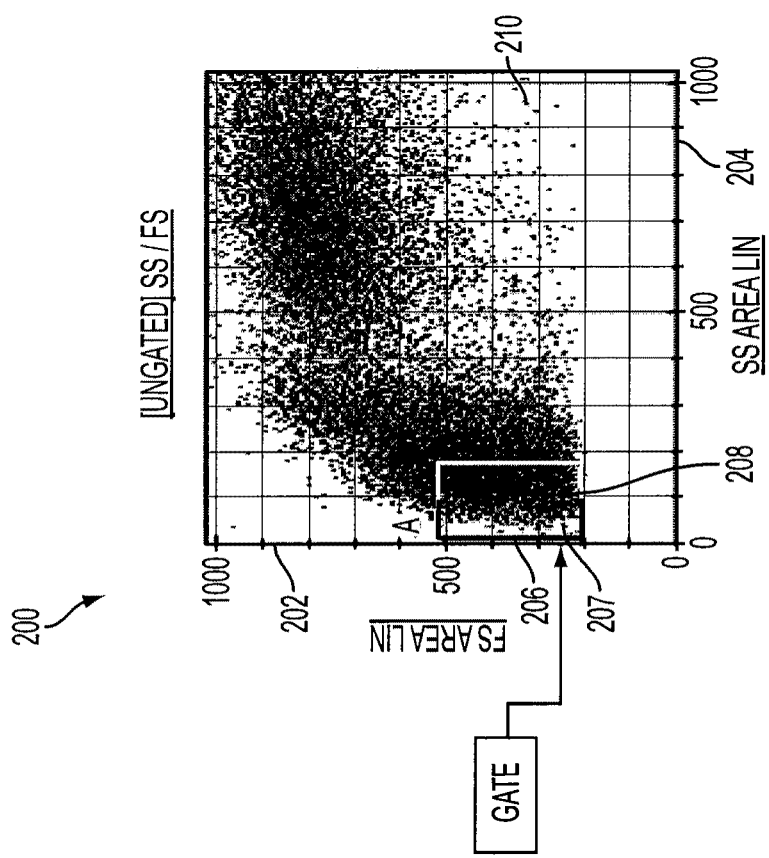
FIG. 2A illustrates an exemplary two dimensional scatter plot graph with one gate.

FIG. 2A illustrates an exemplary two dimensional graph 200, e.g., a scatter plot, which may be used to display flow cytometry data. In the example shown, scatter plot 200 has an X axis 204 scaled to show side scatter values between about 0 and 1,000 and a Y axis 202 scaled to show front scatter values between about 0 and 1,000. In various examples, the scales of the X axis 204 and/or the Y axis 202 may be linear as shown or logarithmic. According to an embodiment of the present invention, scatter plot 200 may be displayed in a graphical user interface (GUI).

In this example, events 210 having X and Y values within the scales of X axis 204 and Y axis 202 are displayed on scatter plot 200. However, events may also be excluded from display in the GUI based on whether they satisfied certain user-selected gates. According to an embodiment of the invention, users select gates on scatter plot 200 by interacting with the displayed scatter plot in the GUI via use of an input device to draw the dimensions and coordinates of gates. In one example, each event 210 may have more than two parameter values. However, only the parameter values corresponding to the parameters associated with X axis 204 and Y axis 202 determine the location or pixel where event 210 is displayed. For the sake of simplicity, the location where event 210 is displayed will be referred to as a pixel. However, this is not intended to limit the display of data such as scatter plot 200 to a particular media or a single pixel, as discussed above. For this example, the term pixel will be used throughout this document as to describe a discrete location on a graph and an associated memory location storing a value or values associated with that discrete location on the graph.

(b) Gating Displayed Data

An exemplary two dimensional gate 207 is shown on scatter plot 200 of FIG. 2A, defined by a first side 206 and a second side 208. As depicted in FIG. 2A, two dimensional gate 207 includes two other sides (not labeled). Some events 210 are inside gate 207, other events 210 are outside gate 207. In accordance with an embodiment of the present invention, a user selects gate 207 on scatter plot 200 by interacting with the displayed scatter plot in user interface 111 via use of input device 115 to draw first side 206 and second side 208. In one example, the use of the terms "inside a gate" and "satisfy a gate" are interchangeable. In one example, a gate may have one or more dimensions. For example, gate 207 is shown having two dimensions: first side 206 defines a Y dimension and second side 208 illustrates an X dimension. In various examples, each gate may be described by any algebraic and/or Boolean combination of, for example, gate values, gate variables, gate conditions, and gate operators. Gate variables can correspond to parameters measured for each event. Gate values may describe limits for the gate variables. Gate conditions may include relational operators, such as less than ("<"), greater than (">"), etc. Gate operators may be Boolean operators, such as "AND" and "OR." The two-dimensional, rectangular gates shown are merely used as simple examples to aid comprehension, but other embodiments are not limited to this example. Because gates may be described by any combination of, for example, gate values, gate variables, gate conditions, gate operators, gates may be any regular or irregular shape. Gates may include any Boolean and/or algebraic construction involving any number of parameters (gate variables). Further, gates may include more than two variables, and may not be displayable on a two dimensional plot. A user may define a gate using a graphical user interface (e.g., drawing or click/drag gate boundaries), by typing in a gate description, or by any other method, including default gates.

In this example, user selected gate 207 may be expressed as "(200<FS Area<510) AND (180>SS Area)." Thus "FS Area" and "SS Area" are gate variables, numbers "200," "510," and "180" are gate values, symbols "<" and ">" are gate conditionals, and "AND" is a gate operator. Events with parameter values that satisfy user selected gate 207 may be displayed inside gate 207. Thus, an event with FS Area=200 and SS Area=100 is inside gate 207. Of course, if gate 207 were instead equivalent to the expression "NOT(200<FS Area<510) OR (180<SS Area)," the events 210 circumscribed by boundaries of gate 207, such as the example event with FS Area=200 and SS Area=100, would be outside gate 207, and the remaining events would be inside gate 207.

In one example, gates may include gate variables corresponding to parameters, which are not displayed on a currently visible scatter plot. For example, event 210 includes parameter values corresponding to the FS Area parameter and the SS Area parameter. It may also have parameter values corresponding to other parameters w, x, y, and z. Thus, a gate may be expressed as "(125<w) AND (445<x<289) OR (z>500)" and event 210 may be inside (or outside) the gate even though the gate is not visible. However, for ease of description, gates are often discussed in conjunction with a display showing the gate. In an embodiment, the display showing gate 207 may be user interface 111.

According to an embodiment of the invention, and with reference to FIGS. 1 and 2A, scatter plot 200 is displayed in user interface 111 by analyzer application 114 and gate 207 is selectable by a user via input device 115 interacting with scatter plot 200 within user interface 111. For example, a user, using input device 115, may define gate 207 using user interface 111 by drawing, selecting, clicking, or dragging gate boundaries 206 and 208. In other embodiments, a user may define gate 207 by other methods including, but not limited to, inputting a gate description or using a default gate established by analyzer application 114.

FIG. 2B illustrates an exemplary scatter plot 220, which has two user-selected gates, gate 222 and gate 223. Some events 210 are inside gates 222 and 223, other events 210 are outside gates 222 and 223. Some events 225 are inside gates 222 and 223.

As with scatter plot 200 depicted in FIG. 2A, scatter plot 220 may be also used to display flow cytometry data. In the example shown, scatter plot 220 has an X axis 204 scaled to show side scatter values between about 0 and 1,000 and a Y axis 202 scaled to show front scatter values between about 0 and 1,000. In various examples, the scales of the X axis 204 and/or the Y axis 202 may be linear as shown in FIG. 2B, or they may be logarithmic (not shown). According to an embodiment of the present invention, scatter plot 220 may be displayed in a graphical user interface (GUI), such as user interface 111.

Gate 222 is shown having two dimensions: first side 226 defines a Y dimension and second side 230 illustrates an X dimension. Gate 223 is also shown having two dimensions: first side 224 defines a Y dimension and second side 228 illustrates an X dimension. In various examples, gates 222 and 223 may be described by any algebraic and/or Boolean combination of, for example, gate values, gate variables, gate conditions, and gate operators.

According to an embodiment of the invention, and with reference to FIGS. 1 and 2B, scatter plot 220 with two gates is displayed in user interface 111 by analyzer application 114 and gates 222 and 223 are selectable by a user via input device 115 interacting with scatter plot 220 within user interface 111. For example, a user, using input device 115, may define gates 222 and 223 using user interface 111 by drawing, selecting, clicking, or dragging gate boundaries 226 and 230; and 228 and 224, respectively. In other embodiments, a user may define gates 222 and 223 by other methods including, but not limited to, inputting gate descriptions or using default gates established by analyzer application 114.

(c) Histograms

Figure 2D:
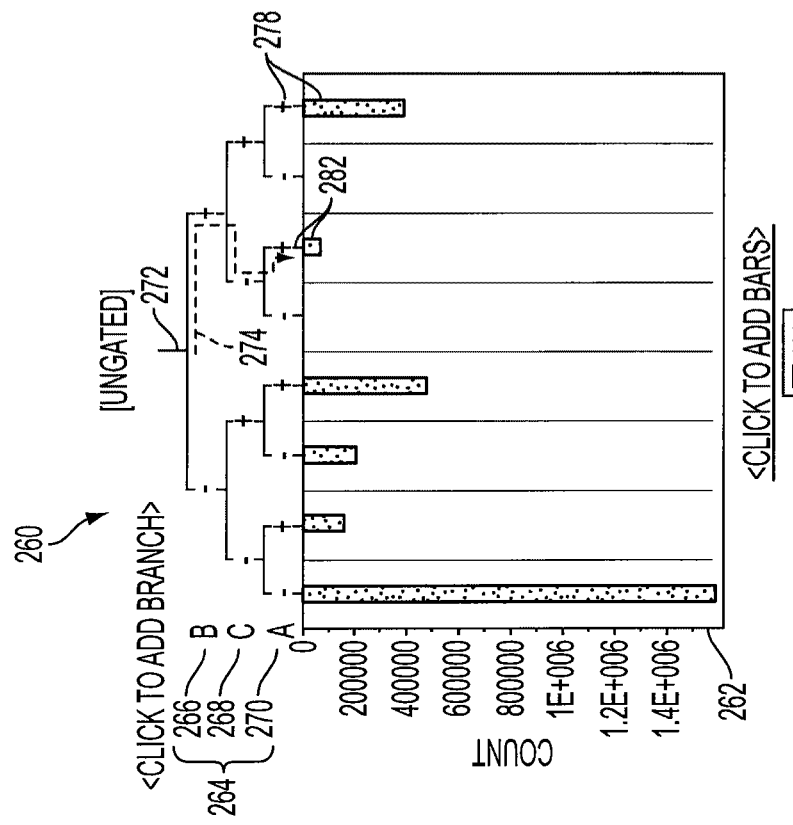
FIG. 2D illustrates an exemplary tree plot.
Figure 2C:
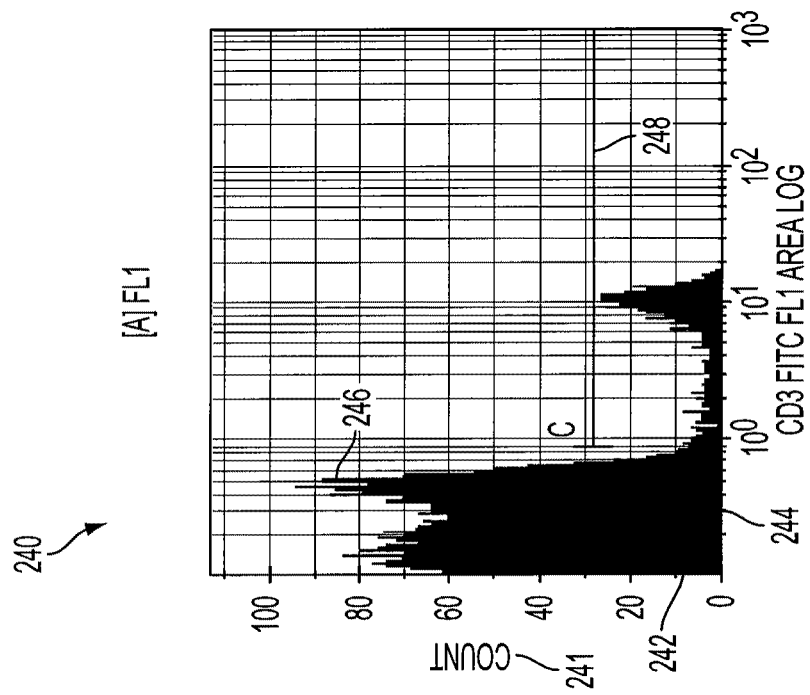
FIG. 2C illustrates an exemplary histogram graph having a logarithmically scaled axis.

FIG. 2C illustrates an exemplary histogram 240 having a gate 248. Gate 248 is a one-dimensional gate (e.g., "FITC FL1 Area>$10^0$"). According to an embodiment of the present invention, a user, using input device 115, can drag or slide one dimensional gate 248 horizontally along the X axis 244 of histogram 240 in order to change the definition of gate 248. Histogram 240 has an X axis 244 logarithmically scaled to show CD3 FITC FL1 Area values from approximately $10^{-1}$ to $10^3$. Histogram 240 also has a Y axis 242 linearly scaled to show a count value from approximately zero to 110. Histogram 240 includes a plurality of bars 246 depicted as bars having a constant width. In this example, the leaf widths are relatively narrow and appear almost as lines. In other examples, histograms may have variable-width leaves. In this example, each bar 246 represents a number of events having a CD3 FITC FL1 Area value falling within a region along X axis 244 defined by the width of the bar 246. In other words, histogram 240 represents a frequency distribution illustrated by bars 246, each bar having a width representing a class interval and having a height representing the number of events falling into the class. The class can conceptualized as a bin of data. For example, the height of bars 246 along Y axis 242 can represent the count of events in an input gate and the width of bars 246 along X axis 244 represent the intervals of the input gates. In an embodiment, the bars in histogram 240 may identify the frequency of positive values for occurrences of certain dyes or markers within input gates of data displayed in histogram 240. For example, one dimensional gate 248 may be used to identify a subpopulation of positive events for specific dyes or markers within the events displayed in histogram 240.

In an embodiment, users, using a selection made with input device 115 can change between counts and percentages of data values on Y axis 242. In an embodiment, the GUI allows users to select a view counts or percentages on Y axis 242. For example, by using input device 115 to interact with a portion of the GUI such a label 241 along Y axis 242, a user can toggle between scaled side scatter values ranging from 0 to 1,000 on Y axis 242 and percentages ranging from 0 to 100% on Y axis 242. The counts displayed in histogram 240 correspond to the number of events in an input gate. According to one embodiment, if a user, using input device 115, clicks on label 241, a menu is displayed that allows the user to select between displaying counts or percentages on Y axis 242. In this way, the user can cause an updated scatter plot (not shown) to be displayed, wherein percentages on the Y axis 242 represent the number of events in a bin divided by the total number of cells depicted in the histogram.

(d) Interactive Tree Plot

FIG. 2D illustrates an exemplary interactive tree plot 260 having an axis 262 linearly scaled to show counts ranging from approximately 0 to 1,600,000. In one example, tree plot 260 may be generated by the processes described elsewhere herein and displayed in the GUI described herein. Tree plot 260 also includes a gate hierarchy 264 comprising levels 266, 268, and 270. Level 266 includes gate B, level 268 includes gate C, and level 270 includes gate A. Gate hierarchy 264 defines branches, such as an exemplary branch 274. In an embodiment, branches of tree plot 260, such as branch 274, can have multiple leaves within a bin of data. Each branch extends from a root 272 to one of a plurality of leaves, such as leaf 278. In an embodiment, leaves, such as leaf 278 in tree plot 260, can be used as an input gate for another plot, such as histogram 240, scatter plot 200, and/or scatter plot 220. Branch 274 extends from root 272 to leaf 282. In tree plot 260 leaves, such as leaf 278. In tree plot 260, each leaf represents a number (count) of events residing in a category defined by a branch (e.g., branch 274). Thus, in this example, leaf 278, represents approximately 200,000 counts in a corresponding category. Leaf 282 represents approximately 70,000 counts in a corresponding category defined by branch 274.

Throughout this document, in the examples discussed, the notation "+" when placed next to a gate means inside the gate, and "−" when placed next to a gate means outside the gate. In tree plot 260, the inside ("+") path is always to the right and the outside ("−") path is always to the left. When reading a gate hierarchy, each branch follows a "+" or a "−" at each level to define the category represented by the leaf at the end of the branch. For example, branch 274 may be read as follows: at level 266, branch 274 follows the "+" path for gate B; at level 268, branch 274 follows the "−" path for gate C; and at level 270, branch 274 follows the "+" path for gate A. Thus, the category delineated by leaf 282 and defined by branch 274 may be described as "B+C−A+," which translates to inside of gate B, outside of C and inside of A. An event is considered to be within this category only if it meets all three of those conditions. In tree plot 260 leaf 282 indicates that approximately 70,000 events were classified in category "B+C−A+" in this example. Throughout this document, the statement that an event "belongs" to a category means that the event should be classified into that category. In one example, classifiers may be phenotypes identified in the data. Phenotypic classifiers include, but are not limited to, cellular characteristics, such as, cellular size, mitotic phase, cellular complexity, and cellular health. Classifiers may also include the presence (or absence) of certain dyes or markers within the data.

Similarly, an event is said to be "binned" when it is determined to which category the event belongs, and an associated bin counter is incremented. In other words, of the classified, measured events in the sample, roughly 70,000 were inside of gate B, outside of gate C, and inside of gate A, and thus belonged to the category "B+C−A+." Similarly, leaf 278 indicates that approximately 400,000 events belonged to category "B+C+A+" in this example. It is important to note that each event will belong to one and only one category, as the categories describe every possible inside/outside combination of the gates. The following sections describe exemplary methodologies and systems which may be used to classify and count events and generate plots such as tree plot 260.

(e) Other Plots

Figure 7:
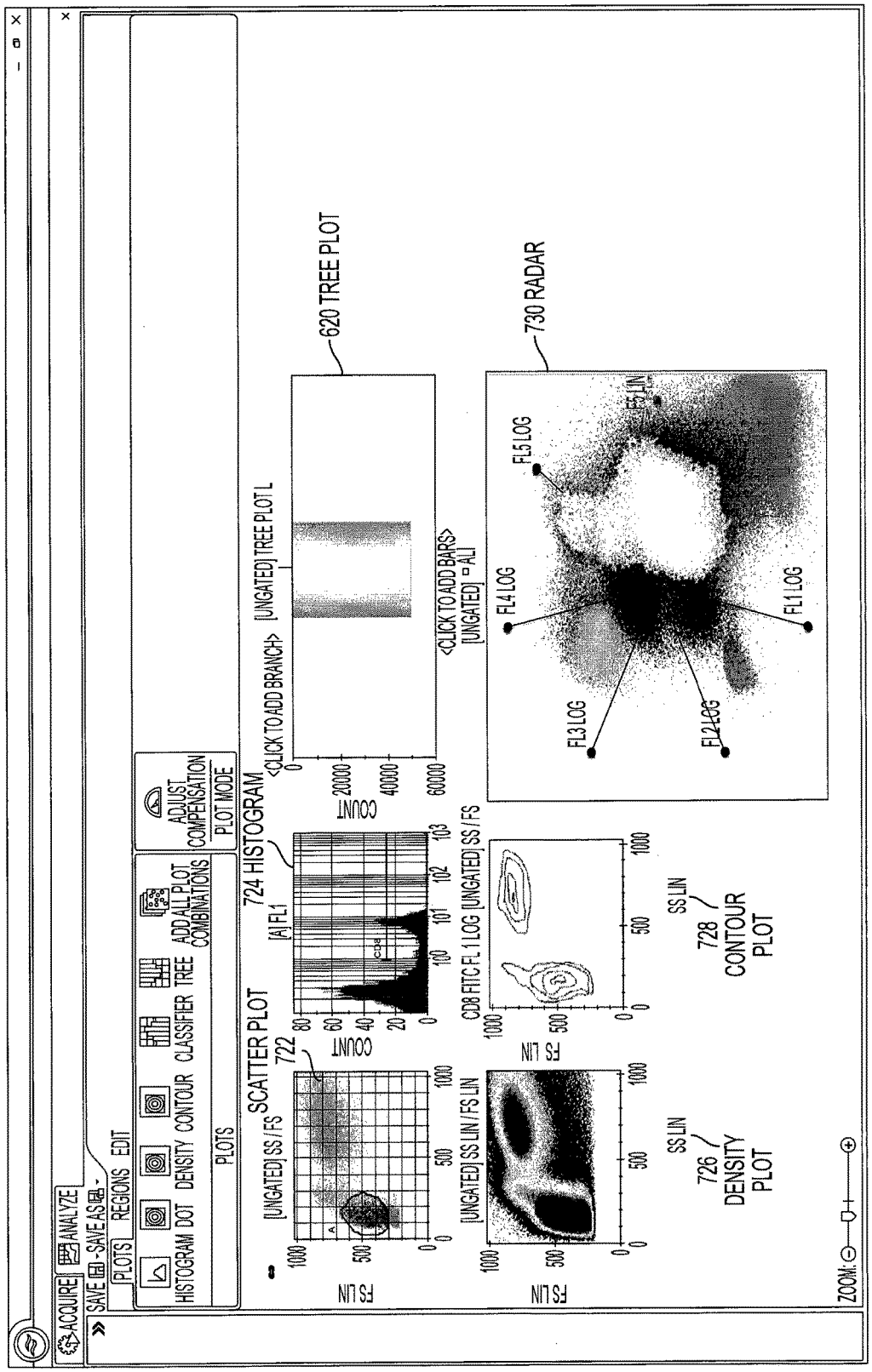
FIG. 7 depicts graphs displayed within an exemplary GUI, in accordance with an embodiment of the invention.

According to embodiments of the present invention, flow cytometry data may be displayed in other plots besides the scatter plots, histograms, and tree plots depicted in FIGS. 2A-D. For example, an additional type of plot is a contour plot. An exemplary contour plot 728 is depicted in FIG. 7. A contour plot can be conceptualized as depicting counts of data where concentric contour lines indicate increasing event counts, which may be similar to how a topographic map depicts changes in elevation with concentric topographic contour lines. Contour plot 728 displays data as bivariate profiles. Contour plot 728 is used for analysis of large numbers of cells in flow cytometry. For example, contour plot 728 can display profiles demonstrating where the majority of events (i.e., cells with a certain phenotype) are in the plot. With contour plot 728, it is possible to show a percentage of the acquired events.

As another example, an additional type of plot displayed by embodiments of the invention is a density plot. An exemplary density plot 726 is depicted in FIG. 7. A density plot 726 displays classified data in 3 dimensions: an X-axis, a Y-axis, and third axis indicating the number of cells in a given X-Y coordinate. Density plot 726 can be used to depict low and high counts of events, such as numbers of cells displaying a certain phenotype. For example, cellular phenotypes can include, for example, cellular size, mitotic phase, health, and dyes or markers in the cells. Colors or varying shading/contrast can be used in density plot 726 to represent the relative density of cells in each X-Y location within density plot 726. For example, one color or shade can represent the highest density of cells, followed by a second color representing cells occurring at a lower frequency.

Another type of plot displayable by embodiments of the invention is a radar plot. An exemplary radar plot 730 is depicted in FIG. 7. Radar plot 730 can be conceptualized as a multidimensional polar transform displaying clusters of data.

4. Tree Plot Data Generation

Figure 3:
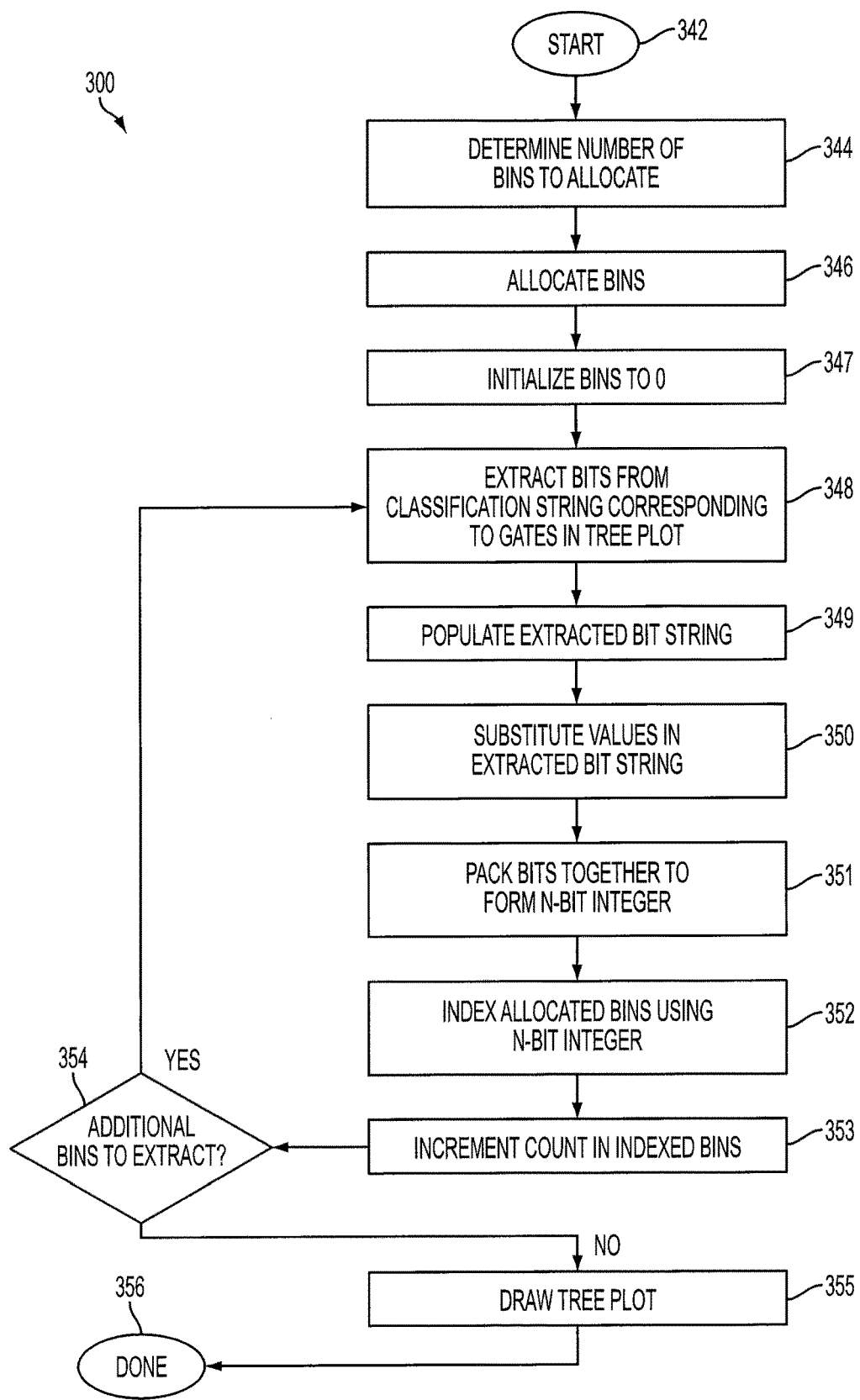
FIG. 3 shows a flowchart illustrating an exemplary tree plot generation process for creating tree plot data.

FIG. 3 shows a flowchart illustrating an exemplary tree plot generation method 300. Method 300 is described with reference to the embodiments of FIGS. 1 and 2D. However, method 300 is not limited to those example embodiments. In the example shown, method 300 illustrates the steps by which tree plot data is created by analyzer application 114. Method 300 is an exemplary plot generation and update process for creating and/or updating, for example, tree plot 260. Note that the steps in method 300 do not necessarily have to occur in the order shown.

In step 342, the process begins with the receipt of data. In an embodiment, the data may be received by analyzer application 114 from FCS files 103 or data miner 113. In another embodiment, the data may be read from an existing tree plot, such as tree plot 260.

In step 344, a tree plot is examined in order to determine the number of bins to allocate. The tree plot examined in this step may be, for example, tree plot 260. In this step the tree plot is examined to determine the number of gates that make up the branches and leaves of the tree plot. For example if there are N gates that make up the branches and leaves of the tree plot, in this step it is determined that $2^N$ bins must be allocated. After the determination is made, the method proceeds to step 346.

In step 346, $2^N$ bins are allocated, where N is a positive integer determined in step 344 relating to the number of gates that make up branches and leaves of the tree plot. After the bins are allocated, the method proceeds to step 347.

In step 347, the bins allocated in step 346 are initialized. Each of the $2^N$ allocated bins have event counters associated with them, and in this step these counters are initially set to 0 (i.e., initialized to 0). Using the example of tree plot 260, each count of events residing in a category is initially set to 0, such that empty leaves are displayed. After initialization is complete, the process continues with step 348.

In step 348, bits are extracted from a classification string corresponding to gates in the tree plot. In this step N bits are extracted from a classification string where the N bits correspond to the N gates identified in step 346. For example, in this step for each event in the classified data, N bits are extracted corresponding to the N gates in the tree plot examined in step 344. In an embodiment, analyzer application 114 extracts the N bits from a classification string received from FCS files 103 or data miner 113. After the N bits are extracted, the process continues with step 349.

In step 349, the extracted N bits from step 348 are used to populate an extracted bit string, and the method continues in step 350.

In step 350, values in the extracted bit string populated in step 349 are substituted with either 0 (true) or 1 (false). In this step, a true value is substituted in the extracted bit string when an event resides in a category and a false value is substituted in the extracted bit string when an event does not reside in a category.

In step 351, after true and false values are substituted in the extracted bit string, the bits are packed together to form an N-bit integer where N corresponds the N gates identified in step 346.

In step 352, the N-bit integer formed in step 351 is used as an index into the $2^N$ bins allocated in step 346. After the bins are indexed, the process continues in step 353. For example, the parameter values corresponding to a gate are located and indexed in this step. After the bins are indexed, the process continues with step 353.

In step 353, the corresponding counter is incremented. In this step the counts in the bins indexed in step 352 are incremented. For example, the parameter values corresponding to a gate are examined and a counter associated with the gate is incremented in this step. Count increments are determined, for example using the parameter values of the events. For example, the counters are incremented depending on the parameter value(s). For example, if a gate found in step 346 is satisfied, the associated counter is incremented.

In step 354, a determination is made whether there are additional bits to be extracted. If yes, then method 300 returns control to step 348 and steps 348-353 are repeated. If no, then method 300 proceeds to step 355.

In step 355, the tree plot is generated (i.e., drawn) using the bin counts incremented in step 353 as the heights for each of the tree plot's leaves. In the example of FIG. 2D, tree plot 260 may be drawn in this step with leaf 282, representing approximately 70,000 counts incremented in step 352 in a corresponding category defined by branch 274. For example, in this step the tree plot is drawn using the bin counts as leaf heights.

In step 356, generating the tree plot data is complete.

5. Exemplary Data Analysis with the User Interface

FIGS. 4-22 illustrate a graphical user interface (GUI), according to an embodiment of the present invention. The GUI depicted in FIGS. 4-22 is described with reference to the embodiments of FIGS. 1-3. However, the GUI is not limited to those example embodiments. For example, the GUI may be user interface 111 of FIG. 1. In an embodiment, system 100 includes an output device configured to control a display on user interface 111 to display the GUI depicted in FIGS. 4-22. In accordance with an embodiment shown in FIGS. 4-22, user interface 111 displays a plurality of interactive plots and statistical reports relating to the displayed plots. System 100 also includes an input device 115, which is configured to allow users to select among respective portions of the plots. For example, through moving a pointer or cursor on the GUI within and between each of the plots displayed in user interface 111 to choose a gate, tree plot leaf, or tree plot branch associated with the selectable characteristic. According to embodiments of the present invention, input device 115 can be, but is not limited to, for example, a pointing device, a track ball, a haptic interface device, a touch pad, a joy stick, a voice activated control system, rotary dials, a touch screen, an eye-based control device, or other input devices 115 used to provide interaction between a user and user interface 111. A haptic interface device refers to an input device 115 which interfaces with a user via the sense of touch by applying forces, vibrations, and/or motions to the user.

According to an embodiment, system 100 includes an output device that is controlled to display the graphical depiction of raw event data 102 in the display of user interface 111 based on using input device 115 to select gates and/or to select characteristics of a plurality of interactive plots and graphs. In another embodiment, system 100 includes an output device that is controlled to display the graphical depiction of data from FCS files 103 in the display of user interface 111 based upon a user using input device 115 to select gates and/or to select characteristics within a plurality of interactive plots and graphs. For example, the output device may be configured to be controlled to display scatter plots, radar plots, contour plots, density plots, histograms, and tree plots corresponding to flow cytometry data in the display of user interface 111.

Figure 4:
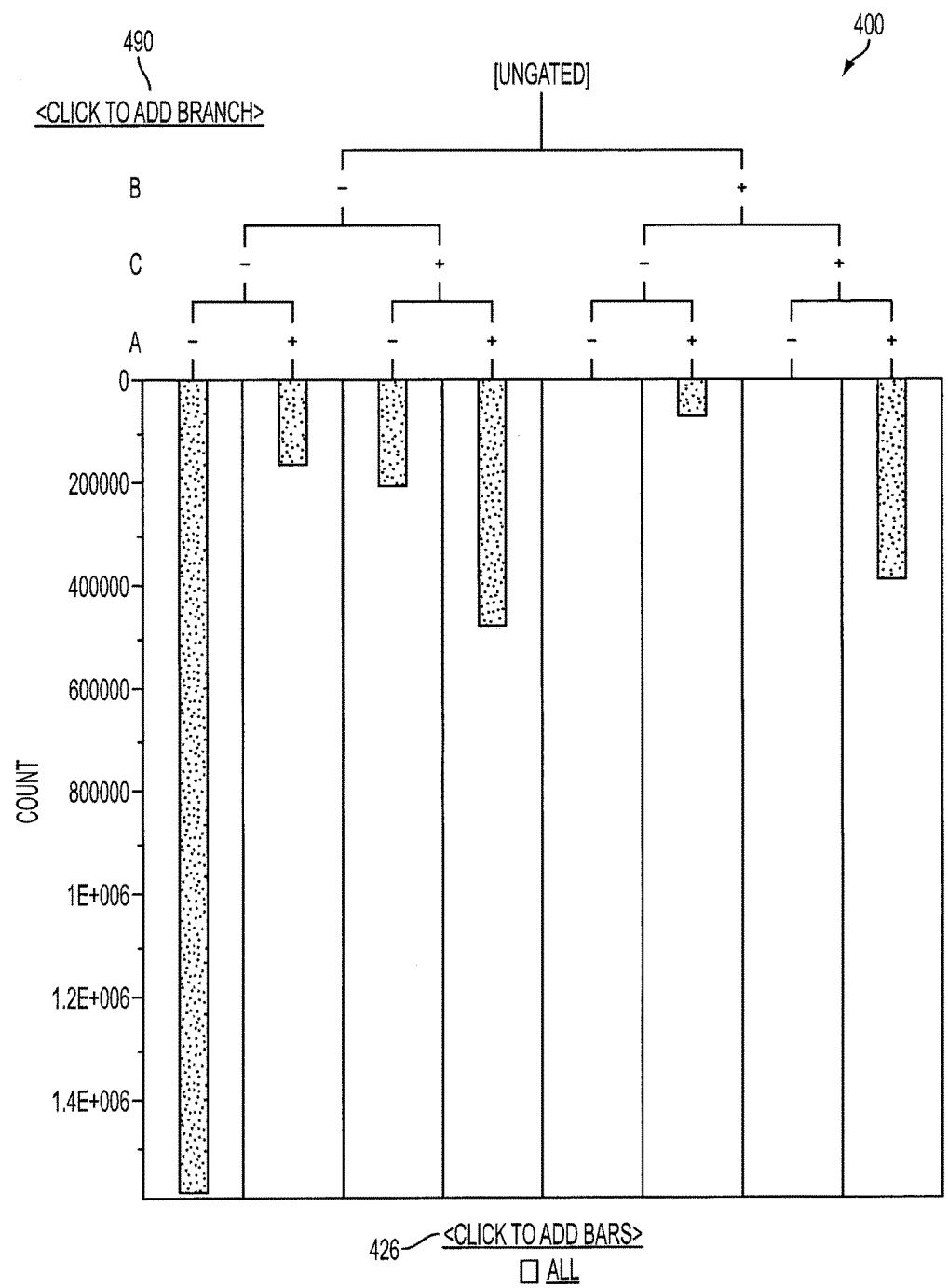
FIG. 4 illustrates an interactive tree plot, in accordance with an embodiment of the invention.

FIG. 4 illustrates how selectable branches are displayed as a selectable characteristic 490 of interactive tree plot 400 of user interface 111. For example, this allows for adding one or more additional branches to the gate hierarchy of tree plot 400. Tree plot 400 includes levels B, C, and A, but additional levels can be added by clicking on selectable characteristic 490. Referring also to FIG. 2D, the GUI allows a user, using input device 115, to interact with selectable characteristic 490 to expand gate hierarchy 264 by adding levels beyond levels 266, 268, and 270, wherein level 266 includes gate B, level 268 includes gate C, and level 270 includes gate A. In this way, the GUI allows a user to expand gate hierarchy 264 to define new branches in tree plot 400, wherein each new branch extends from root 272 to one of a plurality of leaves. In this example, at the bottom of tree plot 400 is second selectable characteristic 426. In the exemplary selectable characteristic 426 Tree plot 400 includes 8 bins with one leaf each, but additional leaves can be added by clicking on selectable characteristic 426. In tree plot 400, each of the 8 bins contain 1 vertical leaf that identifies the event counts for selected subpopulations. According to an embodiment, leaves in interactive tree plot 400 can be used as an input gate for another plot, such as the histograms, scatter plots, contour plots, radar plots, and density plots illustrated in FIGS. 5-20.

Figure 5:
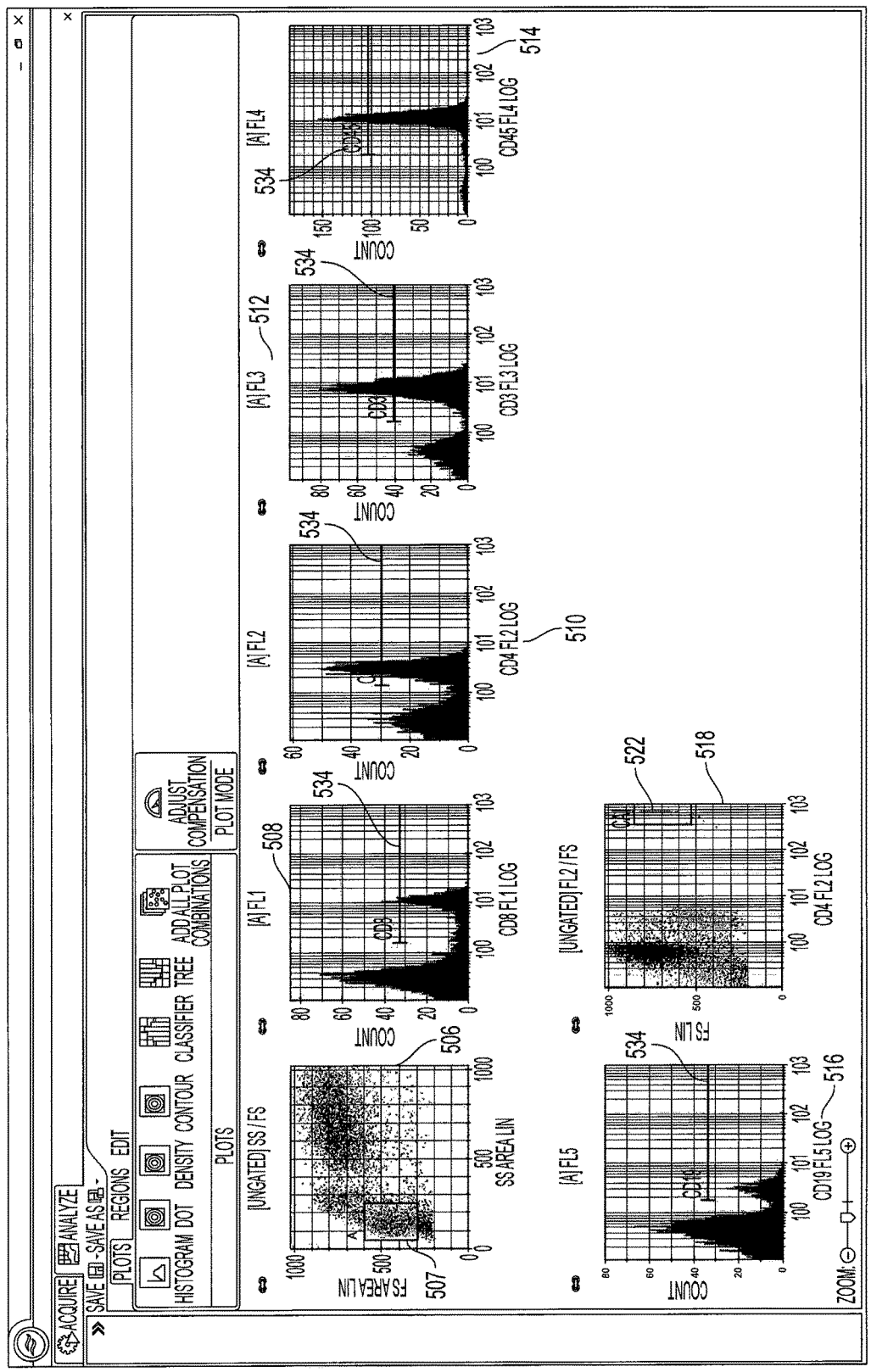
FIG. 5 illustrates an exemplary graphical user interface (GUI), wherein pluralities of graphs are displayed, in accordance with an embodiment of the invention.

FIG. 5 illustrates a plurality of plots displayed in a region of the GUI. In an embodiment, the GUI illustrated in FIG. 5 is user interface 111 as discussed with respect to FIG. 1. In an embodiment, boundaries of gate 534 in histograms 508, 510, 512, 514, and 516, gate 507 in scatter plot 506, and gate 522 in scatter plot 518 are achieved via use of input device 115 to move the sides of gates 507 and 522 and one-dimensional gates 534. According to an embodiment, movement of one-dimensional gates 534 in histograms 508, 510, 512, 514, and 516 is done by using input device 115 to individually drag each respective one of the horizontal one-dimensional gates 534 depicted in the respective histograms. Analyzer application 114 identifies positives (+) for each of the one-dimensional gates 534 in histograms 508, 510, 512, 514, and 516. Positives represent the presence or occurrence of a characteristic within the one dimensional gates 534. In an embodiment, characteristics can be markers, dyes, or phenotypic classifiers. Thus, identified positives (+) may be the occurrence of markers, dyes, or other phenotypic classifiers, and can be used to increment counts of binned data displayed in a tree plot, for example tree plot 621 depicted in FIGS. 6 and 11.

In an embodiment, input device 115 is configured to allow users to select among respective selectable characteristics in scatter plots 506 and 518 and histograms 508, 510, 512, 514, and 516 by moving a pointer or cursor within the plots to choose gates and markers associated with the selectable characteristics in the respective plots.

Figure 6:
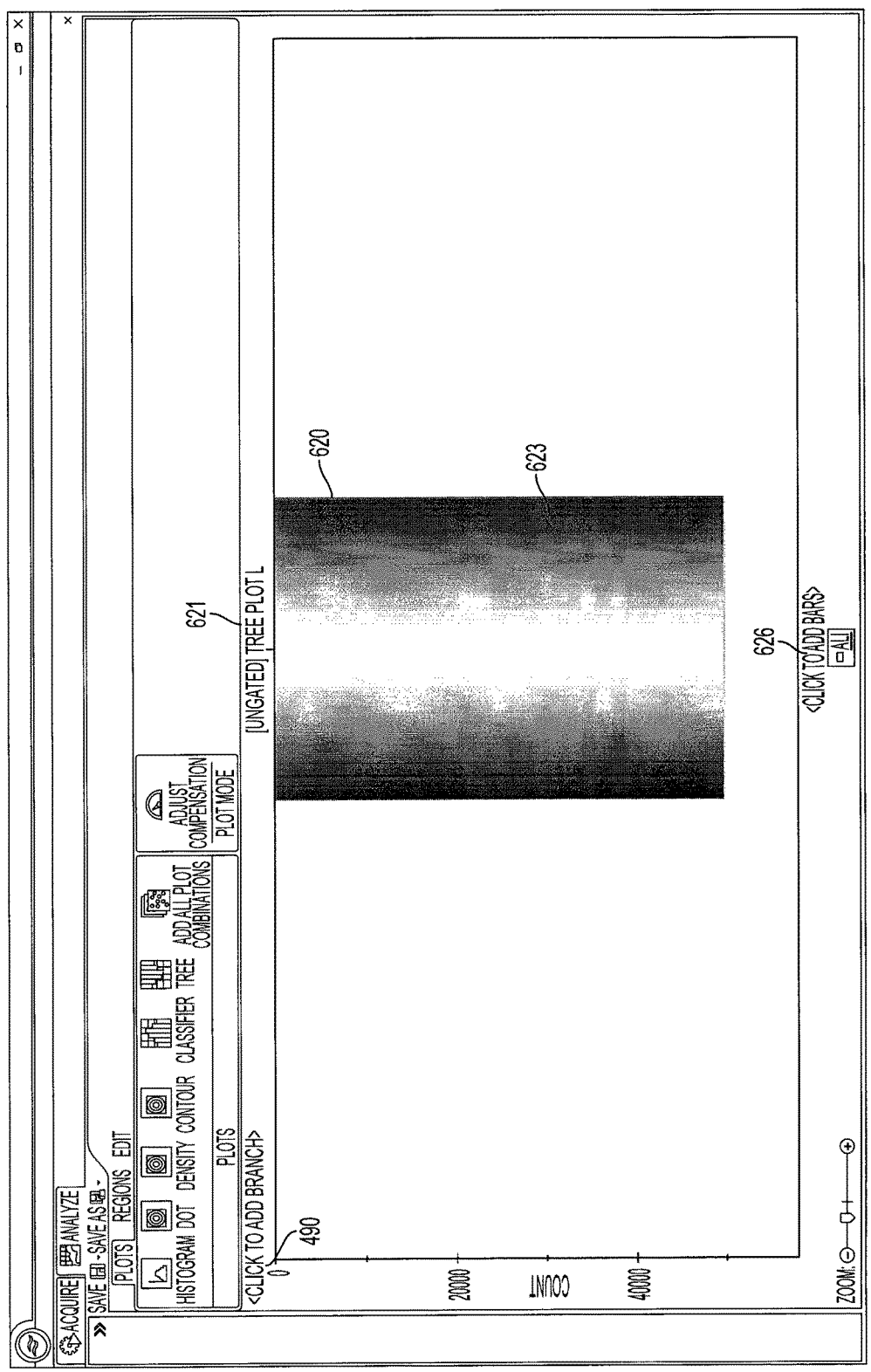
FIG. 6 depicts a tree plot displayed within an exemplary GUI, in accordance with an embodiment of the invention.

FIG. 6 illustrates an un-gated tree plot 620 displayed in the GUI. Tree plot 620 contains a single branch 621 and leaf 623. As described above with reference to FIG. 4, tree plot 620 includes selectable characteristics 490 and 626. Selectable characteristic 490 allows additional branches to be created, and second selectable characteristic 626 allows additional leaves to be created.

FIG. 7 illustrates a plurality of plots displayed in a region of the GUI. In an embodiment, the boundaries of gate A in scatter plot 722 and gate CAL in scatter plot 518 (FIG. 5) are defined via use of input device 115 to move the sides of the gate. According to an embodiment, movement of a one-dimensional gate in histogram 724 is done via use of input device 115 to drag the vertical marker CD8 depicted in histogram 724. Additionally, un-gated tree plot 620 is depicted in FIG. 7. As described below with reference to FIGS. 8-10, un-gated tree plot 620 can be updated via use of input device 115 to define gates 534 in histograms 508, 510, 512, 514, and 516. Similarly, un-gated tree plot 620 may be updated via use of input device 115 to define gate A in scatter plot 722 and/or gate CAL in scatter plot 518 depicted in FIG. 5.

Figure 8:
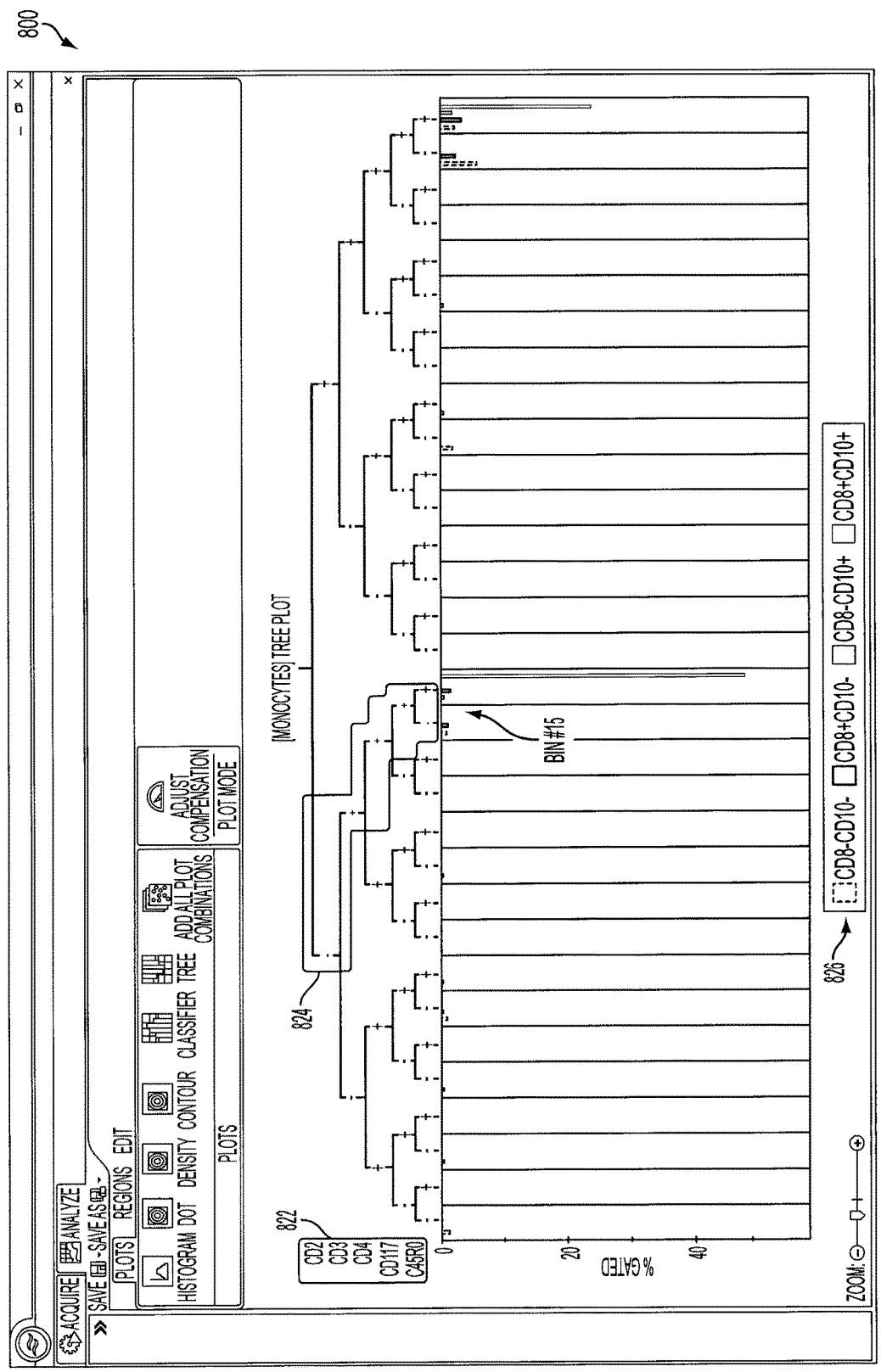
FIGS. 8-10 depict an interactive tree plot displayed within an exemplary GUI, in accordance with an embodiment of the invention.
Figure 9:
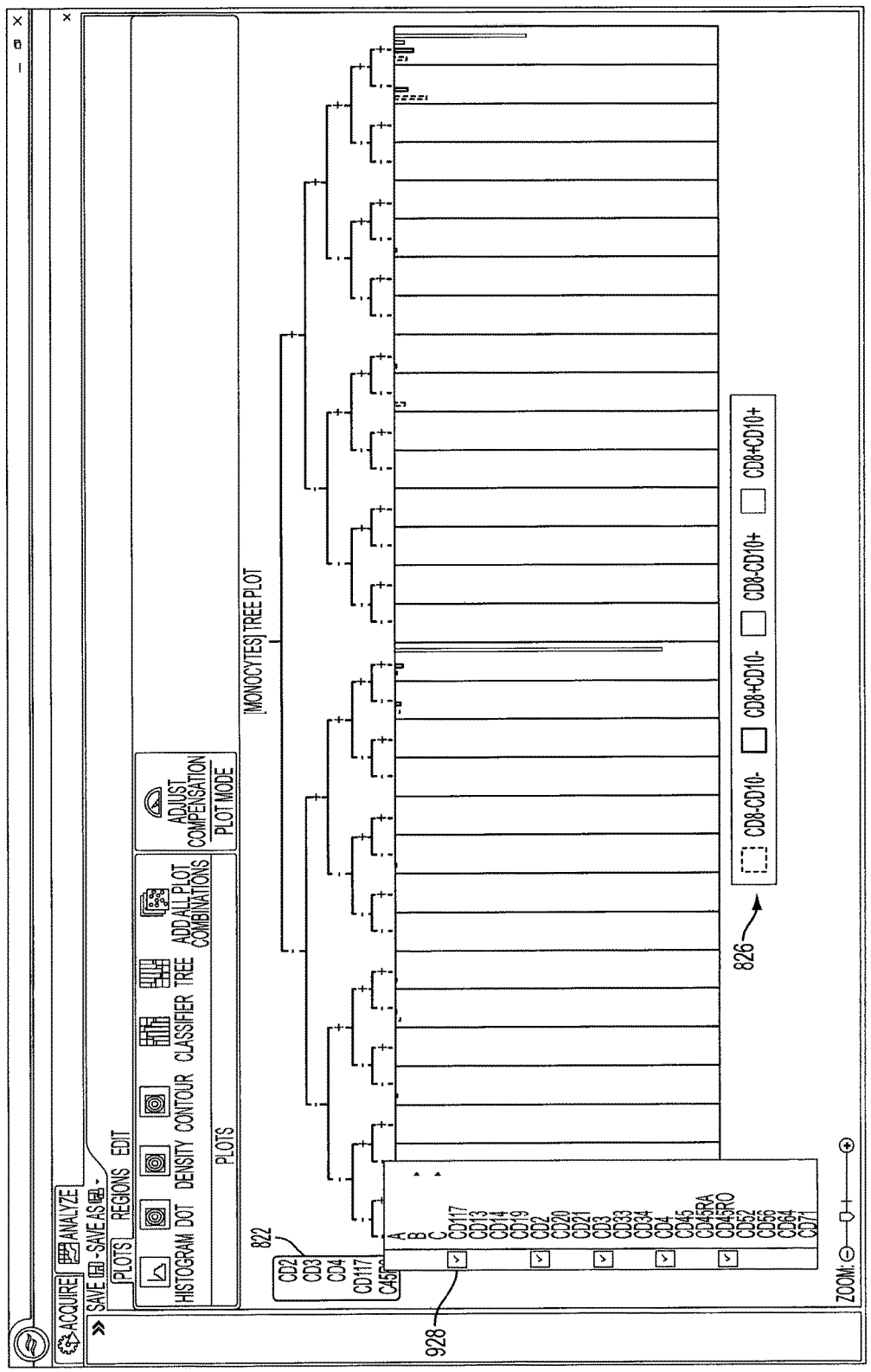
Figure 10:
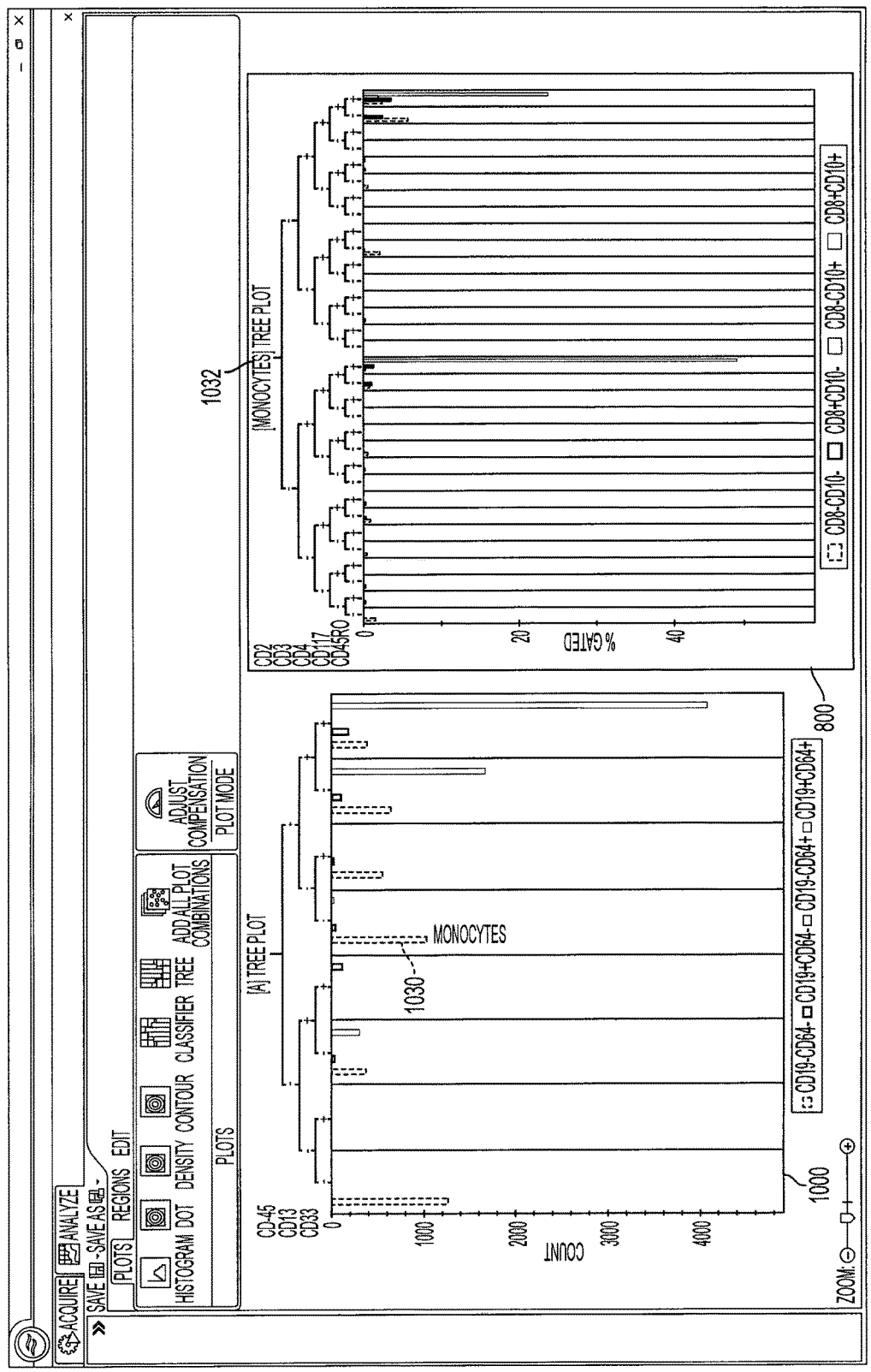

FIGS. 8-10 illustrate an example interactive tree plot 800 that can be displayed in the GUI. In one example, functionality described below can be initiated through a user using input device 115. FIG. 8 illustrates how phenotypic subsets associated with 5+2 or 7 markers can be organized by interacting with selectable characteristics within tree plot 800. At the top of tree plot 800 is the word "Monocytes." In tree plot 800, monocytes is the name of a user-selected gate that isolated the monocyte subpopulation for the data displayed in tree plot 800. Then, in the upper left hand corner of tree plot 800 is first selectable characteristic 822, which allows for markers of interest to be selected. In tree plot 800, markers CD2, CD3, CD4, CD117, and CD45RO are arranged vertically. These markers represent the subpopulations of the monocytes that will be analyzed via interaction with tree plot 800. As there are 5 markers at the top of tree plot 800, there are a total of $2^5$ or 32 sub-phenotype bins in the tree plot.

In this example, at the bottom of tree plot 800 is second selectable characteristic 826. In the exemplary selectable characteristic 826, there are 2 markers labeled CD8 and CD10. In tree plot 800, each of the 32 bins contain 4 vertical leaves that identify the event counts for the CD8−CD10−, CD8+CD10−, CD8−CD10+ and CD8+CD10+ subpopulations. As shown in tree plot 800, some of the bins do not have all leaves because the populations are zero (i.e., the event counts are zero).

Also, in this example, the interactive tree plot 800 contains a third selectable characteristic 824. In an embodiment, as individual bins are interacted with, the marker subpopulation labels are generated in tree plot 800. In this way, bin #15 is associated with the phenotypic label CD2− CD3+ CD4+ CD117+ and CD45RO−. This label within tree plot 800 changes to reflect traversals of individual bins by a user using input device 115.

FIG. 9 illustrates an additional or alternative function of the interactive tree plot 800. The functionality depicted in FIGS. 9 and 10 can be initiated through use of input device 115. Selections of selectable characteristics may be used to change what is being represented within tree plot 800 by changing the markers that are displayed. For example, by selecting any of the selectable characteristics 822 or 826, a pop up menu 928 of all the other markers that were in the protocol is displayed. Similarly, a marker can be de-selected (i.e., un-clicked) from menu 928 to remove the marker from tree plot 800. Also similarly, when adding a marker the new marker can be selected from menu 928. In an embodiment, 2 or more markers can be added to selectable characteristics 822, which causing tree plot 800 to be updated, such that the events are subdivided. In the example of FIG. 9, tree plot 800 subdivides the events generated by the "Monocytes" gate into $2^7$ or 128 sub-phenotypes. Similarly, if another marker is selected using selectable characteristic 826, each of the 128 bins would be subdivided into $2^3$ or 8 subsets.

In FIG. 10, on tree plot 1000 selectable leaf 1030 has a leaf labeled "Monocytes" extending from it. Selectable leaf 1030 leaf in this tree plot can be used as an input gate that isolates the monocyte population. At the top of the tree plot 800, selectable characteristic 1032 represents the "Monocyte" gate that tree plot 800 is gated on. Tree plot 800 is identical to interactive tree plot 800 described above with reference to FIGS. 8 and 9. Tree plot 1000 hierarchically subdivides the events according to the values of CD45, CD13, CD33, CD19, and CD64. Then, one of the leaves (with the corresponding "Monocyte" leaves) acts as an input gate for the tree plot 800 that further subdivides the space according to the values of CD2, CD3, CD4, CD117, CD45RO, CD8 and CD10.

In this way, interaction with tree plots 800 and 1000 displayed in the GUI allows events to be divided into 32 phenotypes, and then one of those bins is subdivided into 128 sub-phenotypes. For example, this can allow for visualization and analyzing of 10, 15, 20, 25, and 30 color assays.

FIGS. 11-20 depict how tree plots are generated an updated using a GUI, such as user interface 111, according to an embodiment of the present invention. Throughout these figures, a similar display is shown with various command regions, which are used to initiate action, files, applications, or other functionality, and multiple plots, e.g., scatter plots, histograms, and an un-gated tree plot. For brevity, only the differences occurring within the figures, as compared to previous or subsequent ones of the figures, is described below.

Figure 11:
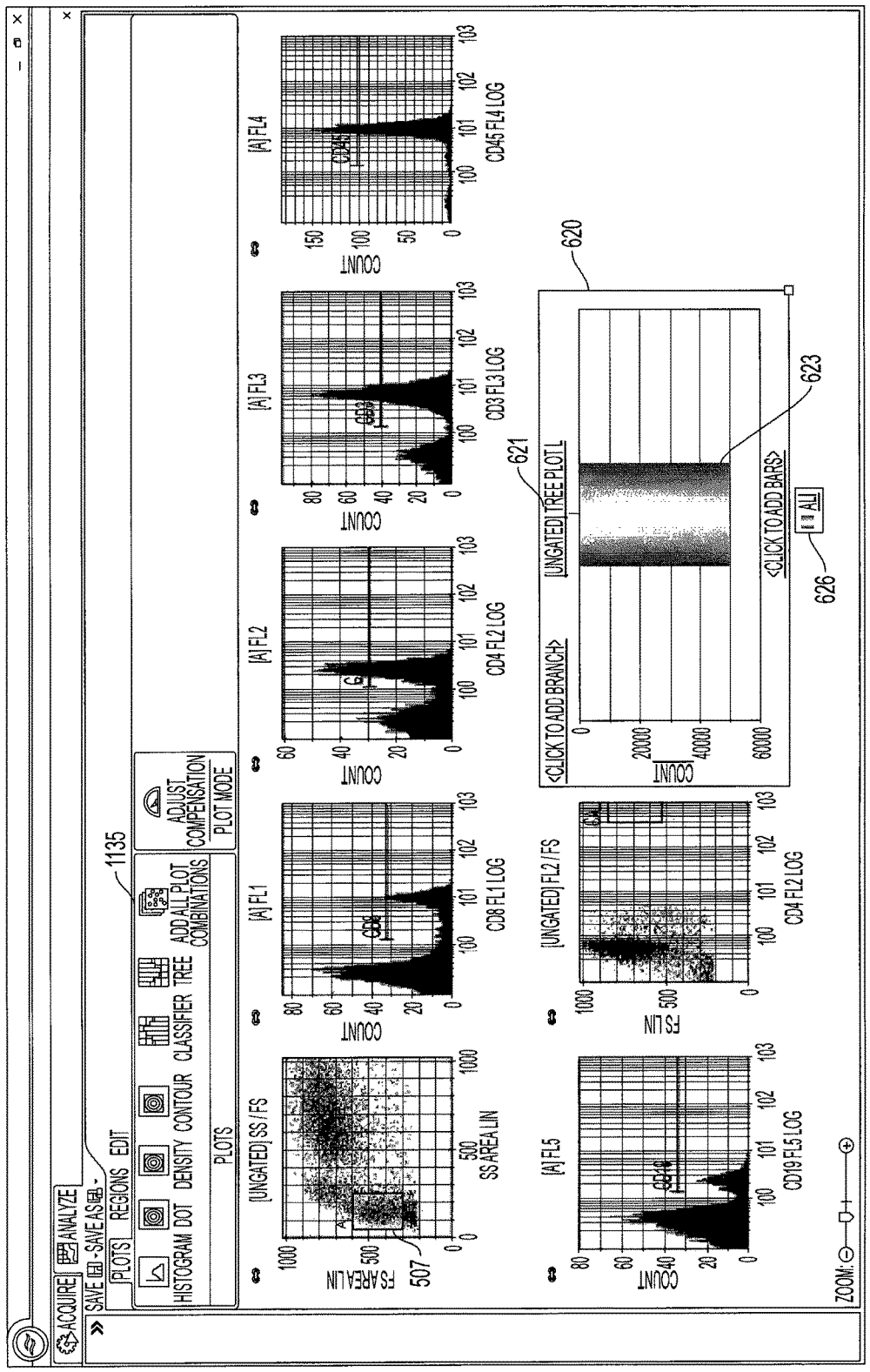
FIGS. 11-20 illustrate a process for generating updated graphs and tree plots within an exemplary graphical user interface (GUI), in accordance with an embodiment of the invention.

As discussed above, FIG. 11 illustrates multiple plots and command regions that can be shown on a GUI to allow for various characteristics to be analyzed. When a command region 1135 is selected, a new, un-gated tree plot 620 is generated. Un-gated tree plot 620 contains a single branch 621 and a single leaf 623 representing event counts. Second selectable characteristic 626 allows additional leaves to be created. Gate 507 depicted in FIG. 11 is not represented in un-gated tree plot 620.

Figure 12:
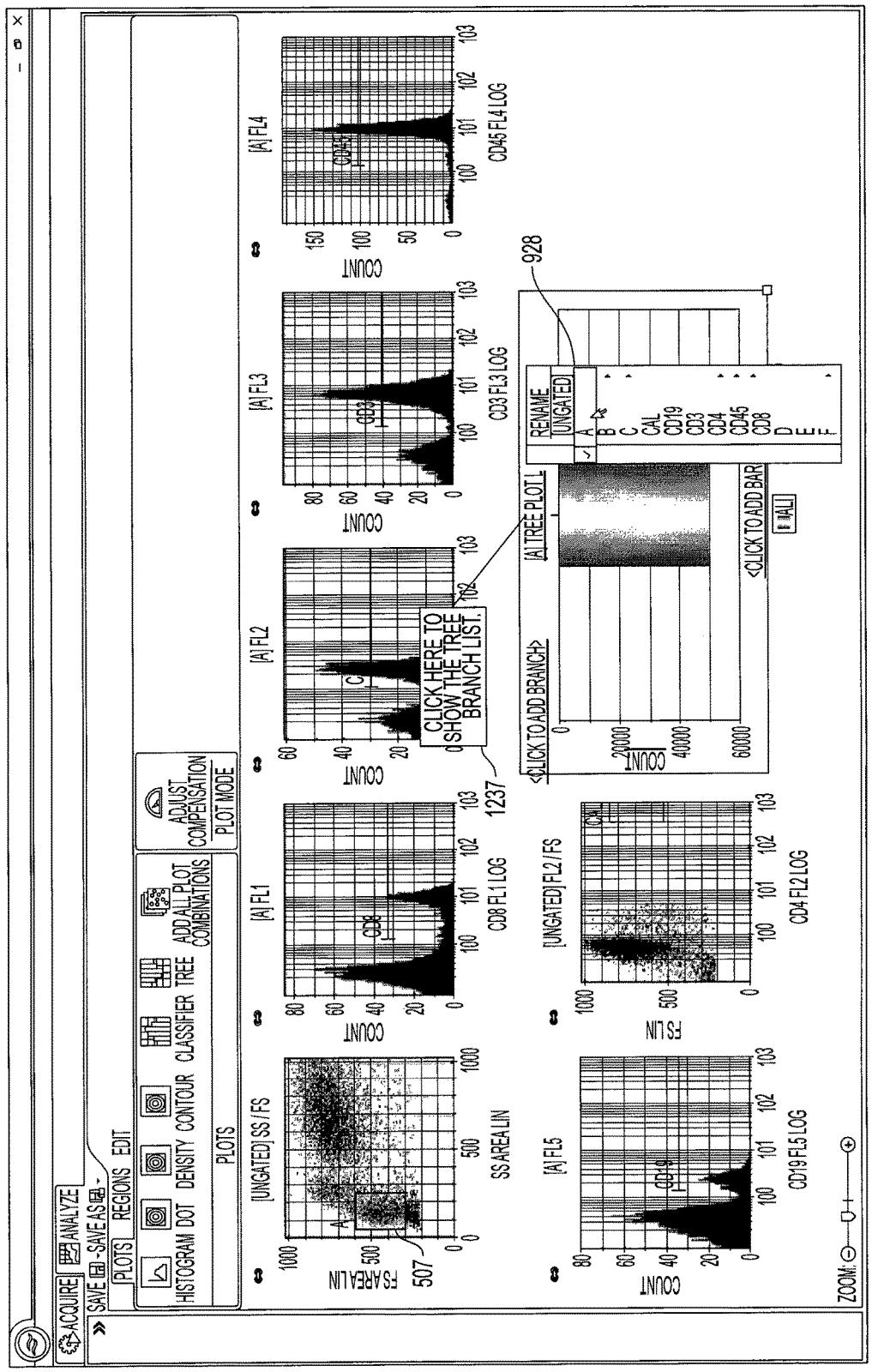

In FIG. 12, if characteristic 1237 is selected, pop-up drop-down menu 928 is displayed to allow a tree plot input gate to be selected. This is similar to the use of pop up menu 928 described above with reference to FIG. 9.

Figure 13:
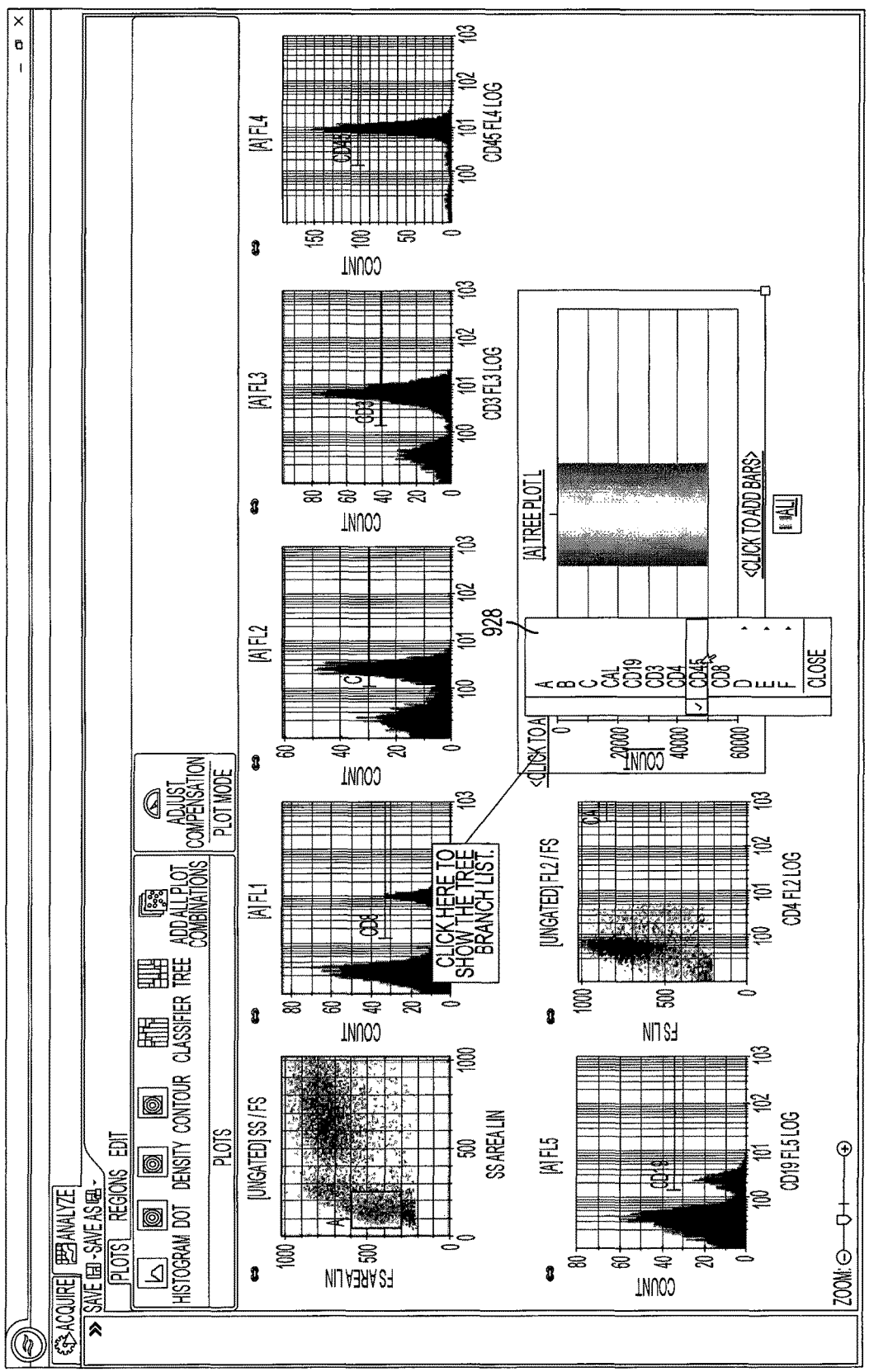
Figure 14:
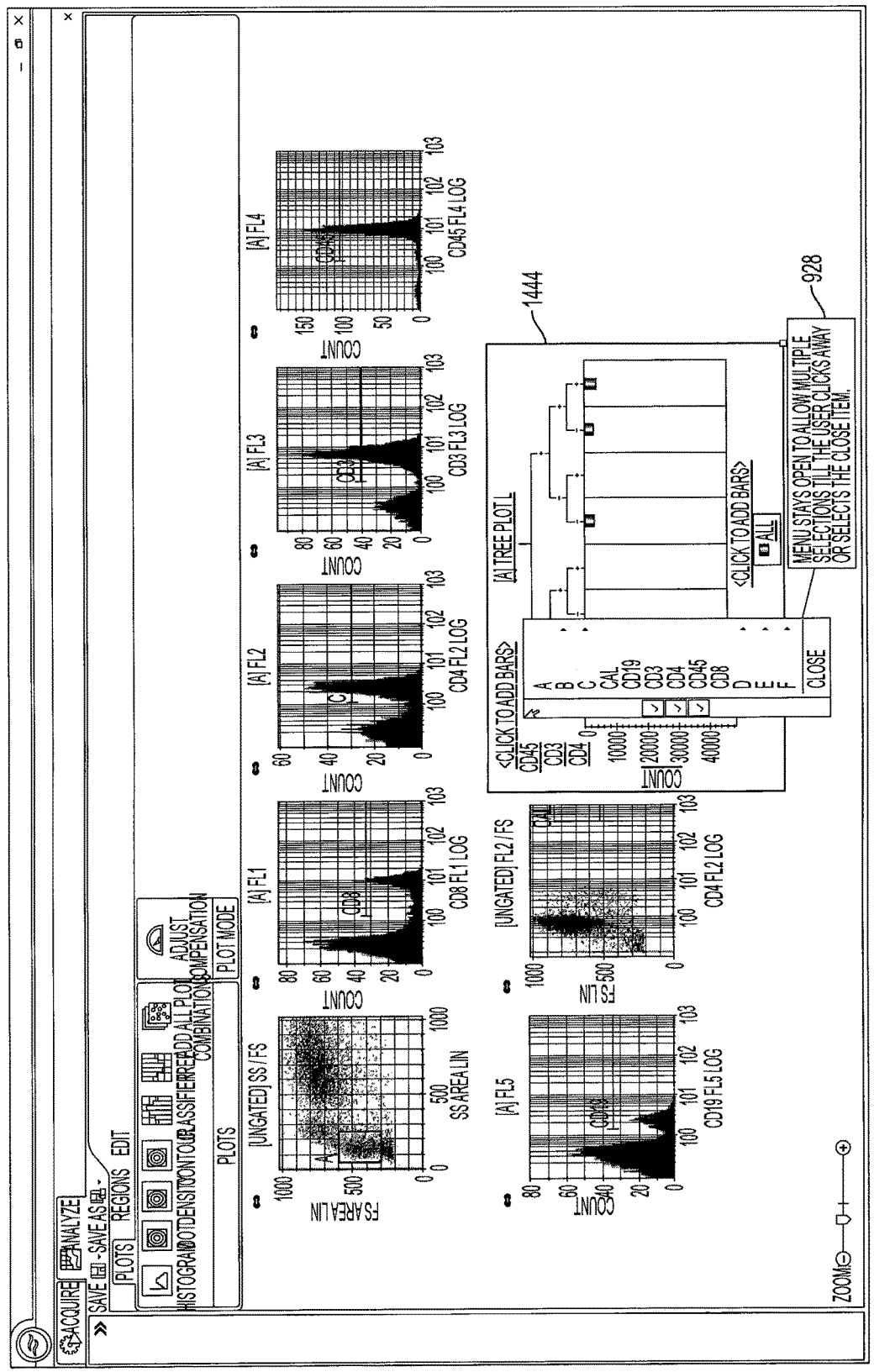

In FIG. 13, characteristics, such as markers, are selected in pop-up drop-down menu 928 to be used as branches for an interactive tree plot, such as tree plot 1444 depicted in FIG. 14.

As shown in FIG. 14, menu 928 remains open to allow a user to make multiple characteristic selections until the user navigates away from menu 928. As additional characteristics are selected in menu 928, tree plot 1444 is updated to reflect the selected characteristics. The characteristics selected in menu 928 may be markers, dyes, or other phenotypes. For example, as markers are added to tree plot 1444 in the order selected from top down in menu 928, tree plot 1444 is substantially immediately updated. Similarly, tree plot 1444 is updated as characteristics are deselected in menu 928.

Figure 15:
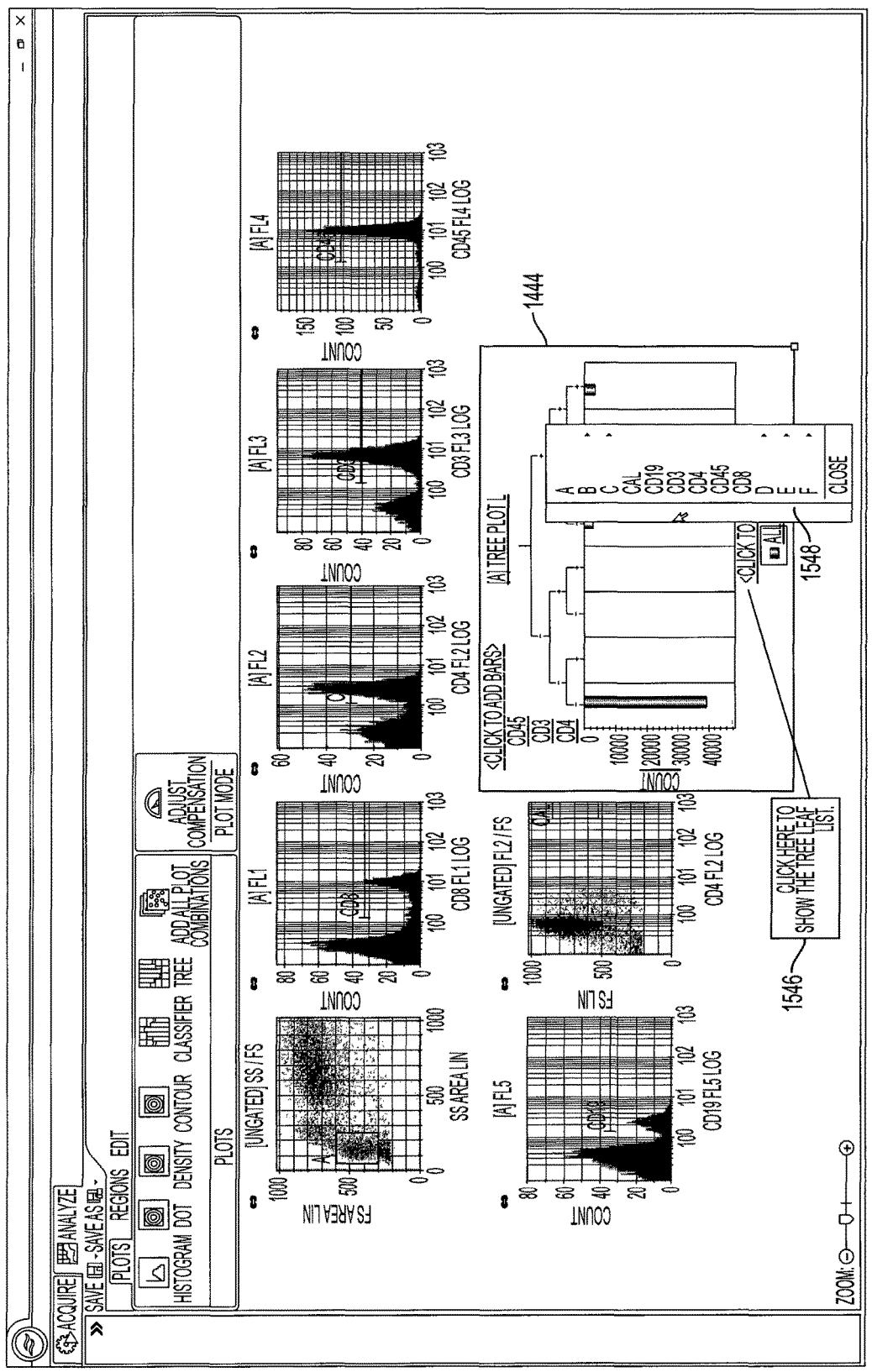

In FIG. 15, selectable characteristics to be used as leaves in tree plot 1444 are selected by a clicking on selectable characteristic 1546 to display the leaf list menu 1548 for tree plot 1444.

Figure 16:
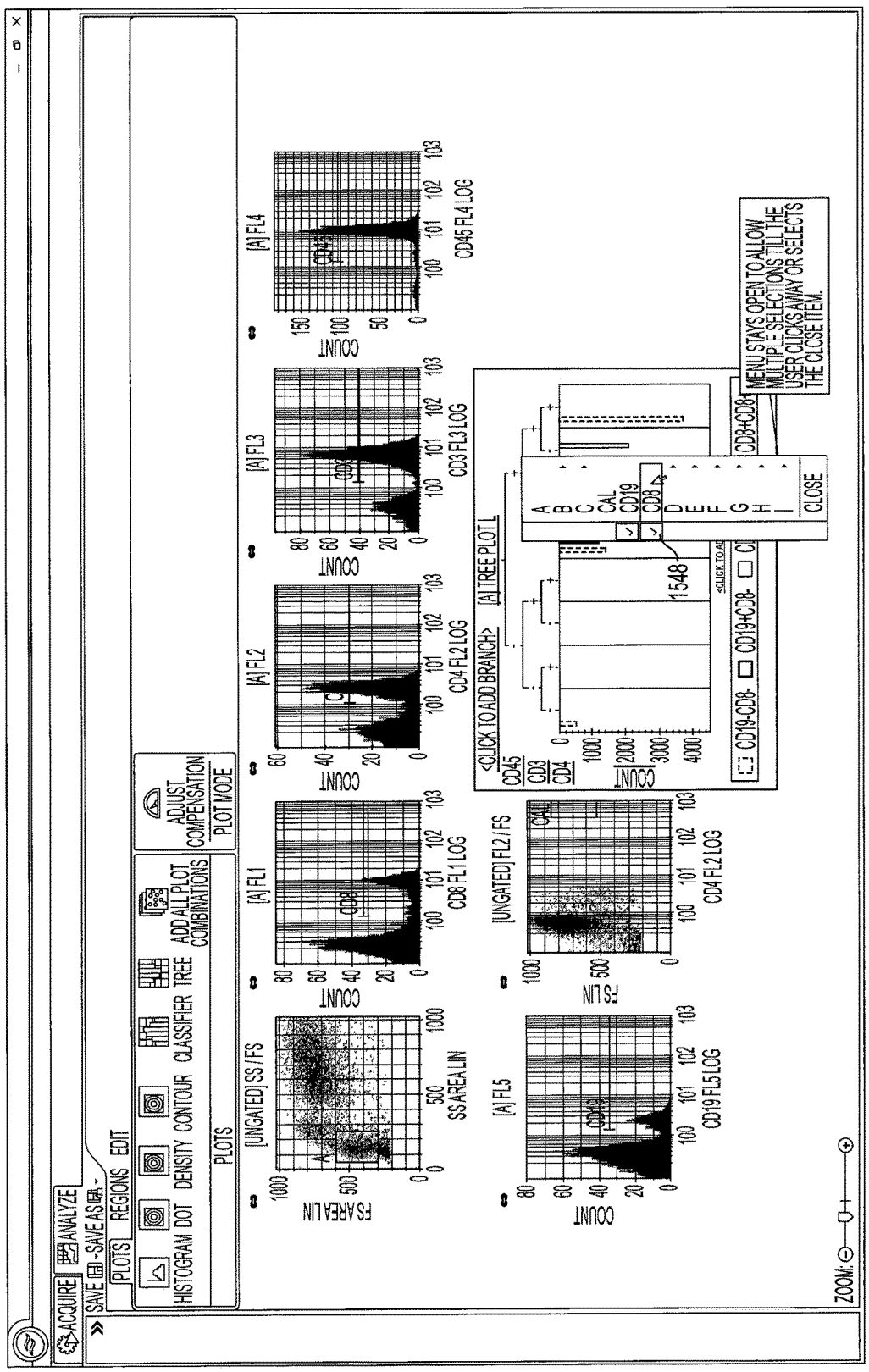

In FIG. 16, menu 1548 remains open to allow multiple leaf selections. Menu 1548 closes when a user navigates away from menu 1548.

FIGS. 17-20 depict the statistics reporting and new plot generation features of analyzer application 114 (FIG. 1), according to an embodiment of the present invention. Throughout these figures, a similar display is shown with various statistics regions, command regions, which are used to initiate action, files, applications, or other functionality, and multiple plots, e.g., scatter plots, histograms, and an un-gated tree plot. For brevity, only the differences occurring within the figures, as compared to previous or subsequent ones of the figures, is described below.

Figure 17:
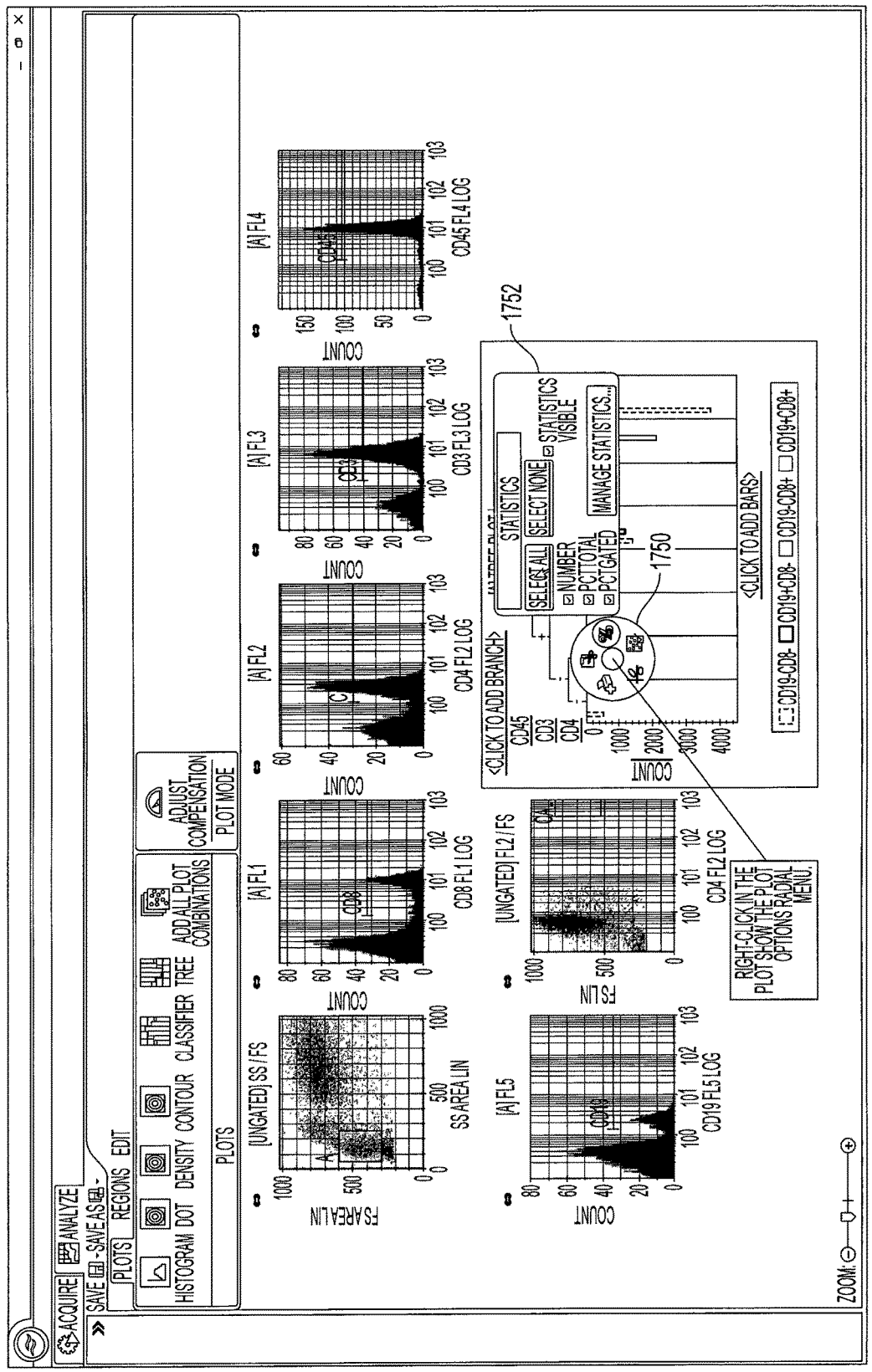

In the example embodiment illustrated in FIG. 17, statistics have been selected to be shown with a tree plot by pressing a right click with the input device to open radial menu 1750. A statistics selection dialog box 1752 is opened based upon user selections in radial menu 1750. Dialog box 1752 displays the range of statistics data corresponding to selections in radial menu 1750 that can be displayed. Boxes can be checked within dialog box 1752 to select or de-select statistics to be viewed. In one embodiment, the statistical data is graphically depicted in a tabular form, as shown in FIGS. 18-20.

Figure 18:
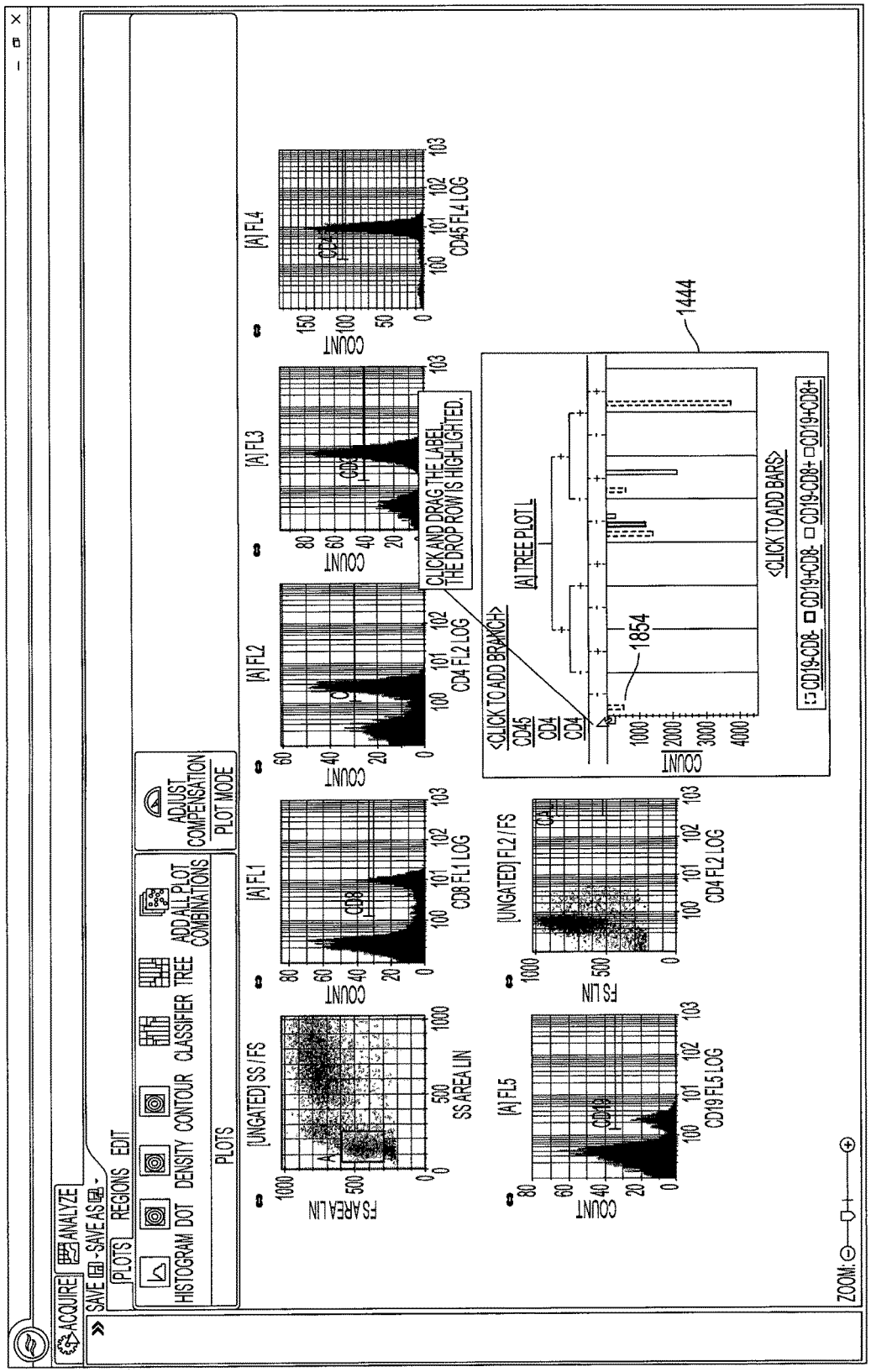

In FIG. 18, characteristics, such as markers in tree plot 1444, can be dragged and dropped in order to rearrange an order of tree plot 1444. This results in tree plot 1444, graph, and statistics being updated immediately by analyzer application 114 (FIG. 1). Label 1854 is selectable by dragging and dropping a highlighted row in tree plot 1444. A tabular statistics report below tree plot 1444 corresponds to the choices made with radial menu 1750 and dialog box 1752.

Figure 19:
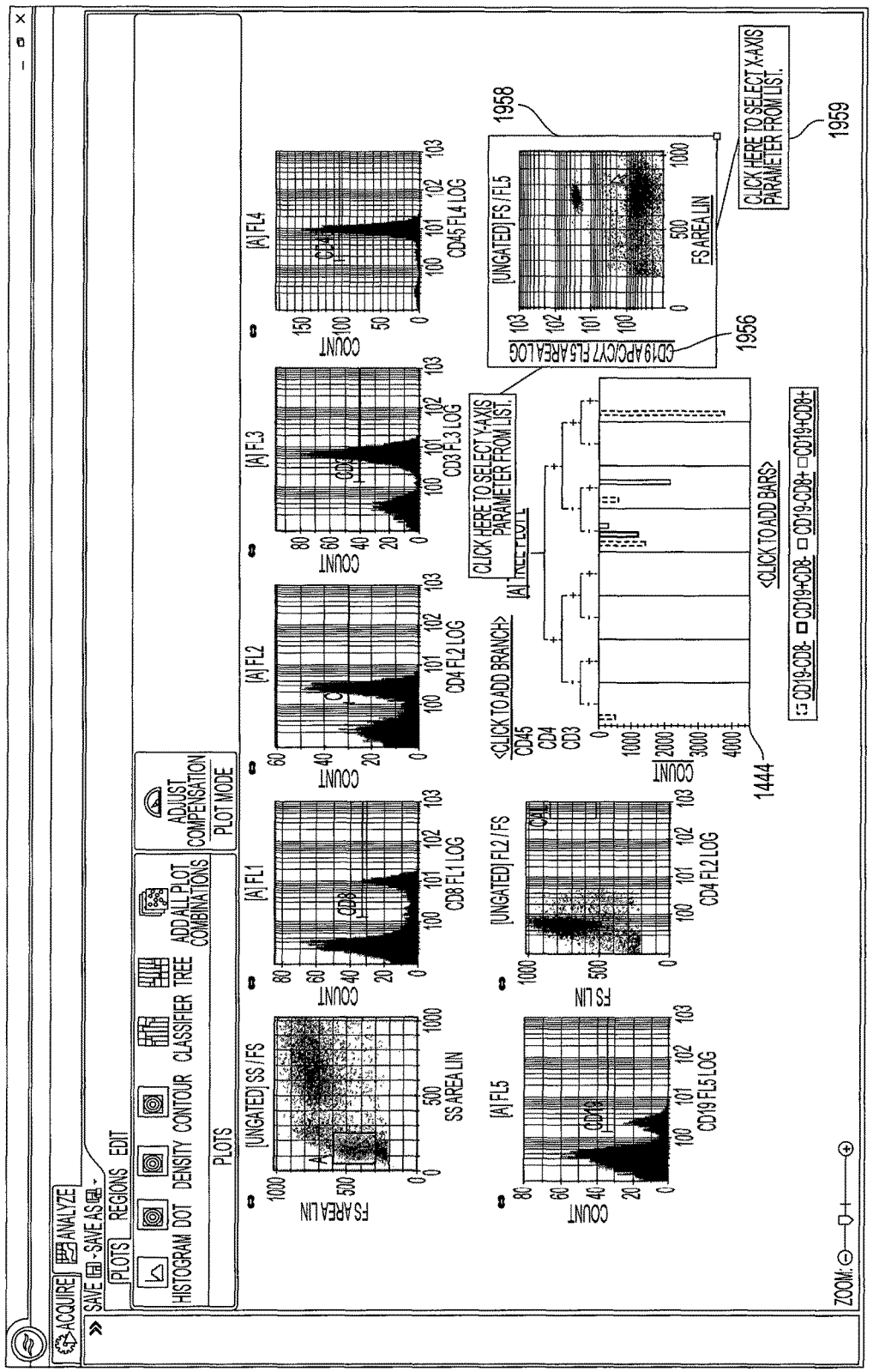

In FIG. 19, while displaying statistics below tree plot 1444, a new scatter plot 1958 is created to allow for continue analysis of data. Scatter plot 1958 is based upon gates of data selected from leaves of tree plot 1444. The Y-axis characteristics 1956 and X-axis characteristics 1959 in newly generated scatter plot 1958 can be selected. In an embodiment, selections of Y-axis characteristics 1956 and X-axis characteristics 1959 are made by clicking on the X and Y axis labels through use of the input device.

Figure 20:
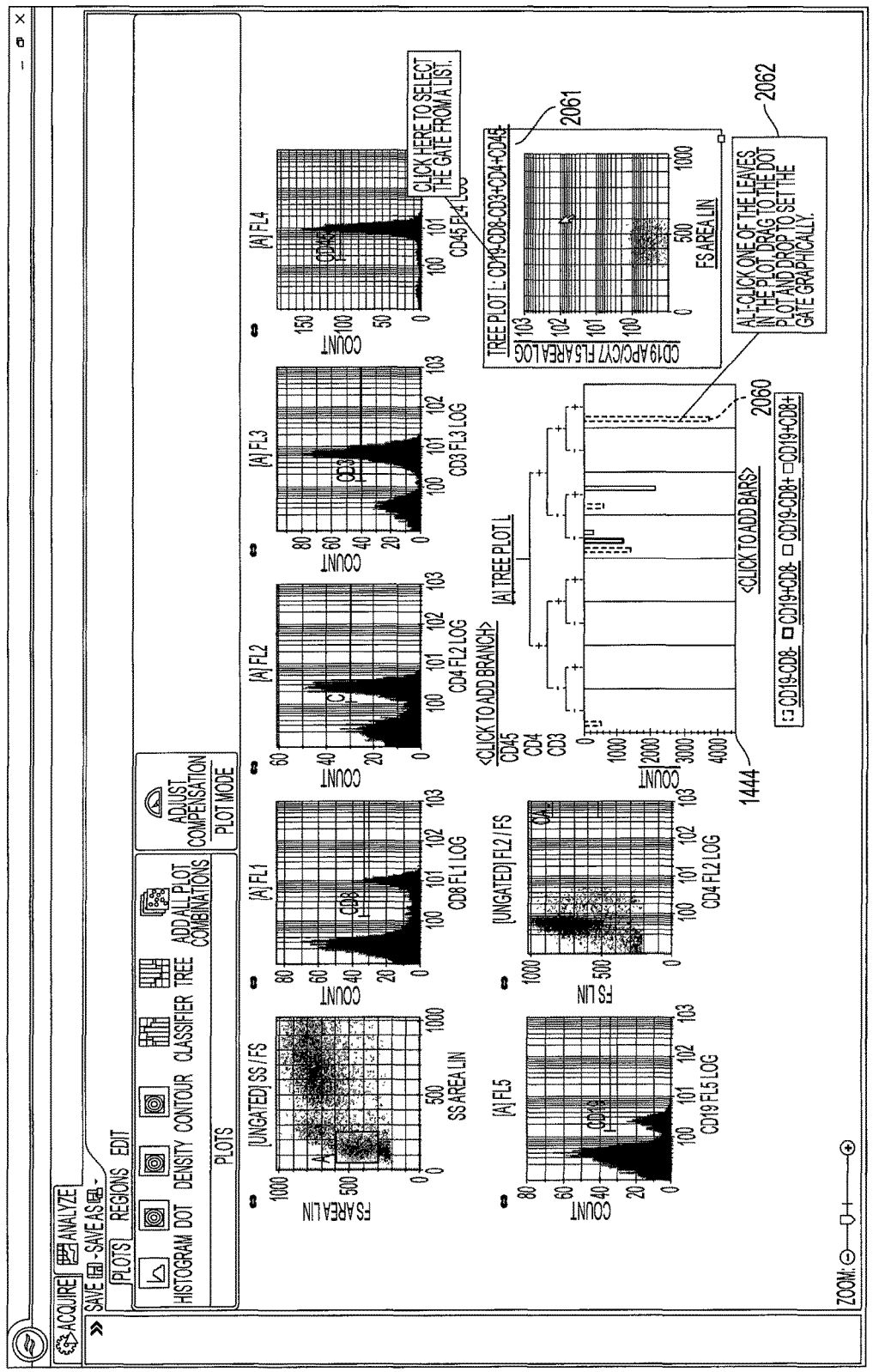

In FIG. 20, one of the leaves in second portion 2060 of tree plot 1444 is selected to gate input to new scatter plot 2062. In the exemplary embodiment depicted in FIG. 20, a user can use the input device to Alt-click on leaf 2060 of tree plot 1444, and drag and drop leaf 2060 into scatter plot 2062 to set the input gate graphically. A user can select gates from a list for scatter plot 2062 by using the input device to click on characteristics label 2061. In embodiments of the invention, the new plot may be any plot type, including another tree plot, and is not limited to being scatter plot 2062 depicted in FIG. 20.

6. Data Display and Analysis Method

Figure 21:
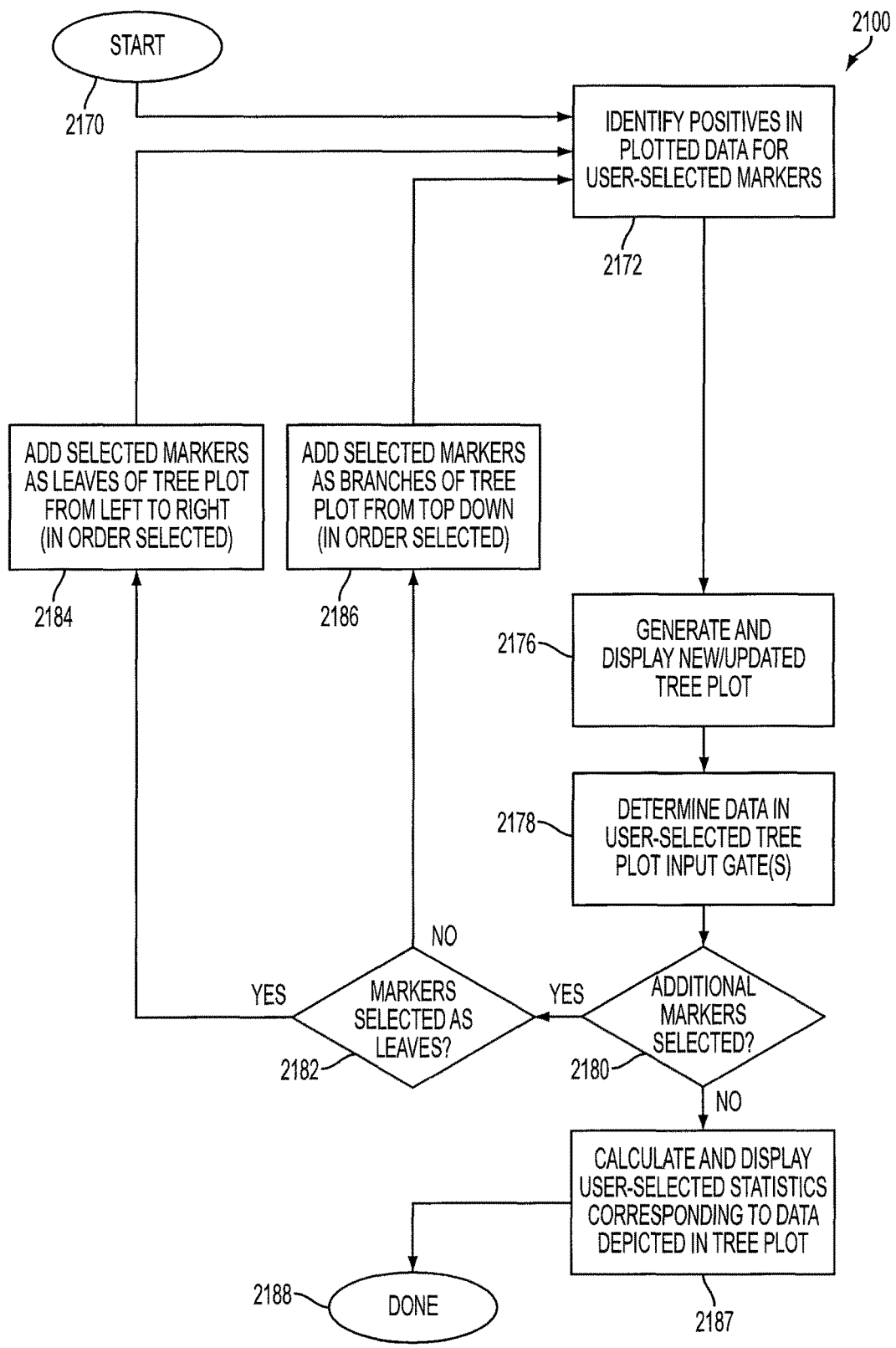
FIG. 21 shows a flowchart illustrating a process for generating and updating a tree plot, in accordance with an embodiment of the invention.

FIG. 21 is a flowchart depicting a method 2100 illustrating steps by which data display and analysis performed, according to an embodiment of the invention.

In the example shown, method 2100 illustrates the steps by which selected data in a user interface is identified and used to generate and update tree plots. Method 2100 is described with reference to the embodiments of FIGS. 1-20. However, method 2100 is not limited to those example embodiments. Note that the steps in method 2100 do not necessarily have to occur in the order shown.

The method begins at step 2170. In an embodiment, step 2170 may consist of analyzer application 114 receiving classified, polychromatic flow cytometer data.

In step 2172, positives are identified for selected markers. In an embodiment, markers may include dyes or other characteristics. In an embodiment, step 2172 may be achieved by use of the exemplary interface depicted in FIGS. 13-16. After positives are identified, method 2100 moves to step 2176.

In step 2176, a new tree plot is displayed. In an embodiment, an interface such as the interface illustrated in FIG. 14 may display new tree plot 1444. If the tree plot already exists, the existing tree plot is updated based upon positives identified in step 2172. For example, if tree plot 1444 already exists, it is updated based upon positives identified in step 2172. After generating or updating the tree plot, method 2100 proceeds to step 2178.

In step 2178, data in selected input gates is determined. Step 2178 may be accomplished via use of the interface depicted in FIG. 20. For example, in this step leaves in tree plot 1444 may be selected as input gates. After selection of input gates, the process continues to step 2180.

In step 2180, a determination is made whether there are additional markers to be selected. If yes, then method 2100 proceeds to step 2182. If no, then method 2100 proceeds to step 2187.

In step 2182, a determination is made whether there markers have been selected as leaves. If yes, then method 2100 proceeds to step 2184. If no, then method 2100 proceeds to step 2186.

In step 2184, selected markers are added as leaves of tree plot 1444 from left to right in order the markers were selected. After markers are added as leaves, method 2100 proceeds to step 2172 and steps 2172-2180 are repeated.

In step 2186, selected markers are added as branches of tree plot 1444 from top down in the order selected. After markers are added as branches, control is passed method 2100 proceeds to step 2172 and steps 2172-2180 are repeated.

In step 2187, selected statistics corresponding to data depicted in tree plot 1444 are determined or calculated and displayed. In an embodiment, statistics can be selected using radial menu 1750 and dialog box 1752 depicted in FIG. 17. After displaying of any selected statistics, the process ends in step 2188.

7. Example Computer Implementation

Figure 22:
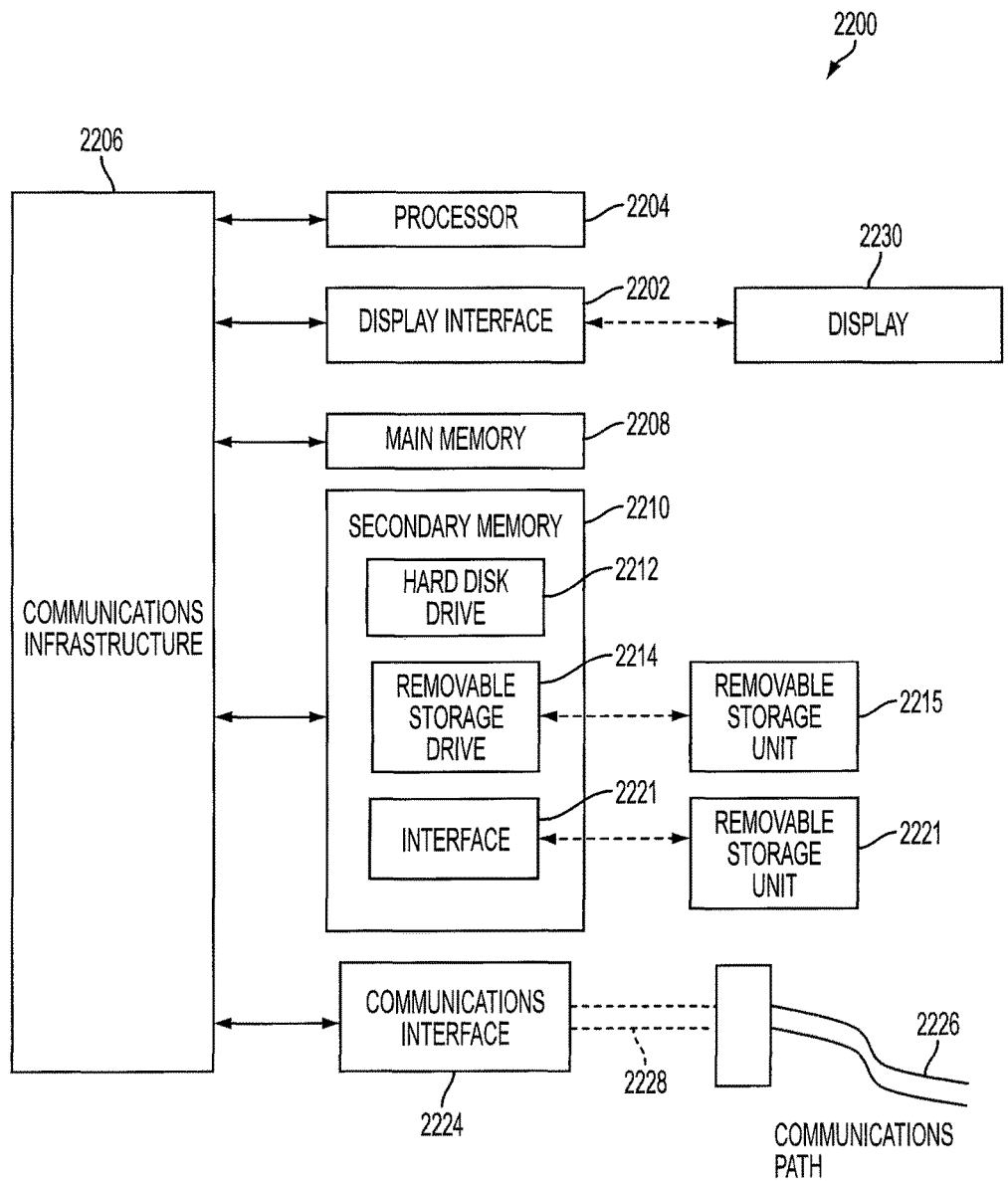
FIG. 22 illustrates an example computer system useful for implementing components of a flow cytometry data display and analysis system, according to an embodiment of the invention.

Various aspects of the present invention can be implemented by software, firmware, hardware, or a combination thereof. FIG. 22 illustrates an example computer system 2200 in which the present invention, or portions thereof, can be implemented as computer-readable code. For example, methods 300 and 2100 illustrated by flowcharts of FIGS. 3 and 21 can be implemented in computer system 2200. Various embodiments of the invention are described in terms of this example computer system 2200. After reading this description, it will become apparent to a person skilled in the relevant art how to implement the invention using other computer systems and/or computer architectures.

Computer system 2200 includes one or more processors, such as processor 2204. Processor 2204 can be a special purpose or a general purpose processor. Processor 2204 is connected to a communication infrastructure 2206 (for example, a bus, or network). Processor 2204 can be a multiprocessor including a plurality of processors (not shown) which can map one or more threads to each processor. Threads of execution, or simply threads, are simultaneous (or pseudo-simultaneous, such as in a multitasking environment) execution paths in any serial or parallel computer. Some threads may execute independently and/or cooperate with other threads. In some parallel architectures, threads may execute on different processors and/or share data (e.g., use shared memory).

For example, in the Compute Unified Device Architecture (CUDA), all threads of a thread block reside on the same processor core, but multiple thread blocks are scheduled in any order across any number of processor cores. The NVIDIA CUDA Compute Unified Device Architecture Programming Guide, Version 2.0 of Jun. 7, 2008, is incorporated by reference herein in its entirety. The number of threads per thread block is limited by the resources available to each processor core. For example, on the NVIDIA Tesla hardware implementation of CUDA, a thread block is limited to 512 threads. Thread blocks are split into warps. Each warp is a set of parallel threads (e.g., 32 threads). A half-warp is the first half or the second half of a warp. Individual threads of a warp start together at the same program address, but may branch and execute independently. Warps are executed one common instruction at a time. If threads of a warp diverge due to a conditional branch, then the threads are serially executed until the threads converge back to the same execution path.

CUDA allows a programmer to define functions, called kernels. Typically a program running on a host such as processor 2204 invokes a kernel. When invoked, a kernel may be executed on a device (not shown) by one or more thread blocks. Therefore, the number of total threads is equal to the number of blocks times the number of threads per block. The programmer may synchronize the execution of the threads in a block by defining synchronization points using a synchronize threads function. All threads of the block wait until all the threads of the block reach the synchronization point before proceeding.

Computer system 2200 also includes a main memory 2208, preferably random access memory (RAM), and may also include a secondary memory 2210. Secondary memory 2210 may include, for example, a hard disk drive 2212, a removable storage drive 2214, flash memory, a memory stick, and/or any similar non-volatile storage mechanism. Removable storage drive 2214 may comprise a floppy disk drive, a magnetic tape drive, an optical disk drive, a flash memory, or the like. The removable storage drive 2214 reads from and/or writes to a removable storage unit 2218 in a well known manner. Removable storage unit 2218 may comprise a floppy disk, magnetic tape, optical disk, etc. which is read by and written to by removable storage drive 2214. As will be appreciated by persons skilled in the relevant art(s), removable storage unit 2218 includes a computer usable storage medium having stored therein computer software and/or data.

In alternative implementations, secondary memory 2210 may include other similar means for allowing computer programs or other instructions to be loaded into computer system 2200. Such means may include, for example, a removable storage unit 2222 and an interface 2220. Examples of such means may include a program cartridge and cartridge interface (such as that found in video game devices), a removable memory chip (such as an EPROM, or PROM) and associated socket, and other removable storage units 2222 and interfaces 2220 which allow software and data to be transferred from the removable storage unit 2222 to computer system 2200.

Computer system 2200 may also include a communications interface 2224. Communications interface 2224 allows software and data to be transferred between computer system 2200 and external devices. Communications interface 2224 may include a modem, a network interface (such as an Ethernet card), a communications port, a PCMCIA slot and card, or the like. Software and data transferred via communications interface 2224 are in the form of signals which may be electronic, electromagnetic, optical, or other signals capable of being received by communications interface 2224. These signals are provided to communications interface 2224 via a communications path 2226. Communications path 2226 carries signals and may be implemented using wire or cable, fiber optics, a phone line, a cellular phone link, an RF link or other communications channels 2228.

In this document, the terms "computer program medium" and "computer usable medium" are used to generally refer to media such as removable storage unit 2218, removable storage unit 2222, and a hard disk installed in hard disk drive 2212. Signals carried over communications path 2226 can also embody the logic described herein. Computer program medium and computer usable medium can also refer to memories, such as main memory 2208 and secondary memory 2210, which can be memory semiconductors (e.g. DRAMs, etc.). These computer program products are means for providing software to computer system 2200.

Computer programs (also called computer control logic) are stored in main memory 2208 and/or secondary memory 2210. Computer programs may also be received via communications interface 2224. Such computer programs, when executed, allow computer system 2200 to implement the present invention as discussed herein. In particular, the computer programs, when executed, allow processor 2204 to implement the processes of the present invention, such as the steps in methods 300 and 2100 illustrated by flowcharts of FIGS. 3 and 21 discussed above. Accordingly, such computer programs represent controllers of the computer system 2200. Where the invention is implemented using software, the software may be stored in a computer program product and loaded into computer system 2200 using removable storage drive 2214, interface 2220, hard drive 2212, or communications interface 2224.

The invention is also directed to computer program products comprising software stored on any computer useable medium. Such software, when executed in one or more data processing device, causes a data processing device(s) to operate as described herein. Embodiments of the invention employ any computer useable or readable medium. Examples of computer useable mediums include, but are not limited to, primary storage devices (e.g., any type of random access memory), secondary storage devices (e.g., hard drives, floppy disks, CD ROMS, ZIP disks, tapes, magnetic storage devices, optical storage devices, MEMS, nanotechnological storage device, etc.), and communication mediums (e.g., wired and wireless communications networks, local area networks, wide area networks, intranets, etc.).

CONCLUSION

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A method for analyzing cell populations in a sample, the method comprising:
    generating, with a flow cytometer, measured values for a plurality of parameters for each of a plurality of cells in the sample, the plurality of parameters for each cell including a first subset of parameters and a second subset of parameters, the second subset of parameters being different than the first subset of parameters;
    for each of the plurality of cells in the sample, determining whether that cell is positive or negative for each parameter in the first subset of parameters;
    displaying an interactive tree plot including a root, levels, branches and leaves, wherein each of the levels corresponds to a respective parameter in the first subset of parameters, wherein each of the levels divides the plurality of cells into a first subset of the plurality of cells which are determined to be positive for the respective parameter and a second subset of the plurality of cells which are determined to be negative for the respective parameter, wherein a path from the root to a first leaf defines a first phenotype based on a branch making up the path, and wherein a height of the first leaf corresponds to a count of cells determined to have the first phenotype;
    receiving a first user input on the interactive tree plot to select or deselect a first parameter from the first subset of the parameters;
    responsive to the first user input, selecting or deselecting the first parameter from the first subset of the parameters;
    responsive to selecting or deselecting the first parameter from the first subset of the parameters, altering the interactive tree plot to reflect an addition or removal of a level corresponding to the first parameter;
    receiving a second user input to select the first leaf of the interactive tree plot; and
    responsive to the second user input, identifying a subpopulation of cells associated with the first leaf, the subpopulation including each cell of the plurality of cells determined to have the first phenotype, analyzing the subpopulation of cells on a second tree plot including second levels to determine a second phenotype for each of the cells in the subpopulation based on the second subset of parameters associated with the second levels, and displaying the second tree plot.

2. The method of claim 1, further comprising:
    measuring a first value for a first measured parameter from the first subset of parameters with a first sensor of the flow cytometer;
    measuring a second value for a second measured parameter from the second subset of parameters with a second sensor of the flow cytometer, the second sensor being different than the first sensor.

3. The method of claim 1, wherein determining whether each cell is positive or negative for a parameter is based, at least in part, on a gate for the parameter.

4. The method of claim 3, wherein each cell is determined to be positive for the parameter when a measured value for the parameter is inside the gate.

5. The method of claim 3, further comprising:
    displaying a third plot of parameters for a plurality of cells in the sample; and
    receiving a third user input indicating a boundary for a gate for one or more of the parameters on the third plot.

6. The method of claim 5, wherein the third plot is a histogram or scatter plot.

7. The method of claim 1, wherein the second tree plot includes a level corresponding to a parameter of the second subset of parameters.

8. The method of claim 1, wherein at least one of the plurality of parameters is a presence of a marker.

9. The method of claim 8, wherein the marker is a cell-surface protein detectable using a labeled antibody, and wherein generating measured values for the plurality of parameters includes measuring fluorescence of the labeled antibody.

10. The method of claim 1, wherein determining whether each cell is positive or negative for a parameter is based, at least in part, on a gate for the parameter, and wherein the cell is determined to be positive for the parameter when the measured value of the parameter is inside the gate.

11. The method of claim 1, wherein a root of the second tree plot corresponds to the first leaf of the interactive tree plot.

12. The method of claim 1, wherein the plurality of parameters include at least one of cellular size, mitotic phase, cellular complexity, and cellular health.

13. The method of claim 1, further comprising:
receiving a third user input on the second tree plot to select or deselect a second parameter of the second subset of parameters;
responsive to the third user input, selecting or deselecting the second parameter from the second subset of the parameters; and
responsive to selecting or deselecting the second parameter from the second subset of the parameters, altering the second tree plot to reflect adding or removing a level corresponding to the second parameter.

14. An apparatus comprising:
a computer processor receiving measured values from a flow cytometer of a plurality of parameters for each of a plurality of cells in a sample, the plurality of parameters including a first subset of parameters and a second subset of parameters, the second subset of parameters being different than the first subset of parameters, and for each of the plurality of cells in the sample, determining whether that cell is positive or negative for each parameter in the first subset of parameters;
a display device in communication with the computer processor, under control of the computer processor, displaying an interactive tree plot including a root, levels, branches and leaves, wherein each of the levels corresponds to a respective parameter in the first subset of parameters, wherein each of the levels divides the plurality of cells into a first subset of the plurality of cells which are determined to be positive for the respective parameter and a second subset of the plurality of cells which are determined to be negative for the respective parameter, wherein a path from the root to a first leaf defines a first phenotype based on a branch making up the path, and wherein a height of the first leaf corresponds to a count of cells determined to have the first phenotype; and
a user input device in communication with the computer processor, the user input device receiving a first user input on the interactive tree plot to select or deselect a first parameter of the first subset of parameters,
wherein the computer processor is further configured to select or deselect the first parameter from the first subset of parameters responsive to the first user input and the display device is further configured to alter the interactive tree plot to reflect an addition or removal of a level corresponding to the first parameter, and
wherein the user input device further receives a second user input to select the first leaf of the interactive tree plot and the computer processor, responsive to the second user input, identifies a subpopulation of cells associated with the first leaf, the subpopulation including each cell of the plurality of cells determined to have the first phenotype, the computer processor, responsive to the second user input, analyzes the subpopulation of cells on a second tree plot including second levels to determine a second phenotype for each of the cells in the subpopulation based on the second subset of parameters associated with the second levels, and the display device displays the second tree plot.

15. The apparatus of claim 14, further comprising the flow cytometer.

16. The apparatus of claim 14, wherein:
the display device further displays a third plot of parameters for a plurality of cells in the sample;
the input device receives user inputs a boundary for a gate for the parameters on the third plot; and
the computer processor determines whether a cell is positive or negative for a parameter of the third plot based, at least in part, on the gate for the parameter.

17. The apparatus of claim 14, wherein the second tree plot includes a level corresponding to a parameter of the second subset of parameters.

18. The apparatus of claim 14, wherein at least one of the plurality of parameters is a presence of a marker, the marker being a cell-surface protein detectable using a labeled antibody, and wherein measurements of the plurality of parameters include measurements of a fluorescence of the labeled antibody.

19. The apparatus of claim 14, wherein:
the input device is further configured to receive a third user input on the second tree plot to select or deselect a second parameter of the second subset of parameters;
the processor is further configured, responsive to the third user input, to select or deselect the second parameter from the second subset of parameters; and
the display device is further configured, responsive to selecting or deselecting the second parameter from the second subset of parameters, to alter the second tree plot to reflect adding or removing a level corresponding to the second parameter.

20. An article of manufacture comprising a non-transitory computer readable storage medium having computer program code recorded thereon, that when executed by a processor, causes a method for analyzing cell populations in a sample to be carried out, the method comprising:
generating with a flow cytometer values for a plurality of parameters for each of a plurality of cells in the sample, the plurality of parameters including a first subset of parameters and a second subset of parameters, the second subset of parameters being different than the first subset of parameters;
for each of the plurality of cells in the sample, determining whether that cell is positive or negative for each parameter in the first subset of parameters;
displaying an interactive tree plot including a root, levels, branches and leaves, wherein each of the levels corresponds to a respective parameter in the first subset of parameters, wherein each of the levels divides the plurality of cells into a first subset of the plurality of cells which are determined to be positive for the respective parameter and a second subset of the plurality of cells which are determined to be negative for the respective parameter, wherein a path from the root to a first leaf defines a first phenotype based on a branch making up the path, and wherein a height of the first leaf corresponds to a count of cells determined to have the first phenotype;
receiving a first user input on the interactive tree plot to select or deselect a first parameter from the first subset of parameters;

responsive to the first user input, selecting or deselecting the first parameter from the first subset of parameters;

responsive to selecting or deselecting the first parameter from the first subset of the parameters, altering the interactive tree plot to reflect an addition or removal of a level corresponding to the first parameter;

receiving a second user input to select the first leaf of the interactive tree plot; and responsive to the second user input, identifying a subpopulation of cells associated with the first leaf, the subpopulation including each cell of the plurality of cells determined to have the first phenotype, analyzing the subpopulation of cells on a second tree plot including second levels to determine a second phenotype for each of the cells in the subpopulation based on the second subset of parameters associated with the second levels, and displaying the second tree plot.

21. The article of manufacture of claim 20, wherein the method further comprises:

displaying a third plot of parameters for a plurality of cells in the sample;

receiving user inputs indicating a boundary of a gate for the parameters on the third plot; and determining whether a cell is positive or negative for a parameter is based, at least in part, on the gate for the parameter.

22. The article of manufacture of claim 20, wherein at least one of the plurality of parameters is a presence of a marker, the marker being a cell-surface protein detectable using a labeled antibody, and wherein measurements of the plurality of parameters include measurements of fluorescence of the labeled antibody.

23. The article of manufacture of claim 20, wherein the method further comprises:

receiving a third user input on the second tree plot to select or deselect a second parameter of the second subset of parameters;

responsive to the third user input, selecting or deselecting the second parameter from the second subset of parameters; and responsive to selecting or deselecting the second parameter from the second subset of parameters, altering the second tree plot to reflect adding or removing a level corresponding to the second parameter.

* * * * *